(12) United States Patent
Pattison et al.

(10) Patent No.: US 9,833,350 B2
(45) Date of Patent: Dec. 5, 2017

(54) ANCHORABLE SIZE-VARYING GASTRIC BALLOONS FOR WEIGHT LOSS

(71) Applicant: EZ-OFF WEIGHTLOSS, LLC, Leawood, KS (US)

(72) Inventors: Mary Pattison, Kansas City, MO (US); Charles Phillip Pattison, Kansas City, MO (US); Stephen J. Lowry, Kansas City, MO (US); Mark Molos, Kansas City, MO (US)

(73) Assignee: EZ-OFF WEIGHTLOSS, LLC, Leawood, KS (US)

( * ) Notice: Subject to any disclaimer, the term of this patent is extended or adjusted under 35 U.S.C. 154(b) by 333 days.

(21) Appl. No.: 14/554,677

(22) Filed: Nov. 26, 2014

(65) Prior Publication Data

US 2015/0150699 A1 Jun. 4, 2015

Related U.S. Application Data

(63) Continuation-in-part of application No. 14/216,666, filed on Mar. 17, 2014, now Pat. No. 9,554,932, and (Continued)

(51) Int. Cl.
A61F 5/00 (2006.01)

(52) U.S. Cl.
CPC ............ *A61F 5/003* (2013.01); *A61F 5/0036* (2013.01); *A61F 5/0069* (2013.01); (Continued)

(58) Field of Classification Search
CPC .............................. A61F 5/0076; A61F 5/0079
See application file for complete search history.

(56) References Cited

U.S. PATENT DOCUMENTS

| 4,315,513 A | 2/1982 | Nawash et al. |
| 4,356,824 A | 11/1982 | Vasquez |

(Continued)

FOREIGN PATENT DOCUMENTS

| WO | WO2011/004335 | 1/2011 |
| WO | WO2015/020977 | 8/2014 |
| WO | WO2014/145799 | 9/2014 |

OTHER PUBLICATIONS

International Search Report and Written Opinion Corresponding to International Application No. PCT/US2014/030625, dated Aug. 1, 2014.

(Continued)

*Primary Examiner* — Tatyana Zalukaeva
*Assistant Examiner* — Kai Weng
(74) *Attorney, Agent, or Firm* — Lathrop Gage LLP

(57) ABSTRACT

Provided herein are balloon systems and related methods for the treatment of obesity. The system includes a transabdominal gastric cannula and size-varying balloons that, with the assistance of the cannula(s) and anchors, are specially positioned and anchored to the gastric wall. The size-varying balloon may have an annulus that in combination with reliable and precise balloon positioning, minimizes the risk of gastric obstruction during use. A malabsorption sleeve may be positioned in the small intestine to further restrict caloric intake through the small intestine. The specially-configured gastric cannula provides a platform for accessing the gastric environment that facilitates precise handling, manipulation, and placement of balloons, including an annular-shaped balloon, in the gastric environment, including by balloon anchors connecting the balloon wall to the lumen-facing stomach wall.

22 Claims, 23 Drawing Sheets

Related U.S. Application Data a continuation-in-part of application No. PCT/US2014/030625, filed on Mar. 17, 2014.

(60) Provisional application No. 61/790,709, filed on Mar. 15, 2013, provisional application No. 61/862,463, filed on Aug. 5, 2013.

(52) U.S. Cl.
CPC .......... *A61F 5/0076* (2013.01); *A61F 5/0079* (2013.01); *A61F 5/0083* (2013.01); *A61F 5/0089* (2013.01)

(56) References Cited

U.S. PATENT DOCUMENTS

| | | | |
|---|---|---|---|
| 4,668,225 A | 5/1987 | Russo et al. |
| 5,007,900 A | 4/1991 | Picha et al. |
| 5,071,405 A | 12/1991 | Piontek et al. |
| 5,112,310 A | 5/1992 | Grobe |
| 5,147,316 A | 9/1992 | Castillenti |
| 5,167,627 A | 12/1992 | Clegg et al. |
| 5,259,399 A | 11/1993 | Brown |
| 5,527,280 A | 6/1996 | Goelz |
| 5,716,347 A | 2/1998 | Gibbs et al. |
| 5,720,734 A | 2/1998 | Copenhaver et al. |
| 5,865,816 A | 2/1999 | Quinn |
| 5,993,473 A | 11/1999 | Chan et al. |
| 6,030,361 A | 2/2000 | Miyashiro |
| 6,419,670 B1 | 7/2002 | Dikeman |
| 6,454,785 B2 | 9/2002 | De Hoyos Garza |
| 6,551,270 B1 | 4/2003 | Bimbo et al. |
| 6,907,992 B2 | 6/2005 | McMichael et al. |
| 6,910,581 B2 | 6/2005 | McMichael et al. |
| 7,025,791 B2 | 4/2006 | Levine et al. |
| 7,122,058 B2 | 10/2006 | Levine et al. |
| 7,220,284 B2 | 5/2007 | Kagan et al. |
| 7,267,694 B2 | 9/2007 | Levine et al. |
| 7,314,489 B2 | 1/2008 | McKenna et al. |
| 7,316,716 B2 | 1/2008 | Egan |
| 7,329,285 B2 | 2/2008 | Levine et al. |
| 7,347,875 B2 | 3/2008 | Levine et al. |
| 7,476,256 B2 | 1/2009 | Meade et al. |
| 7,563,254 B2 | 7/2009 | Delegge |
| 7,678,068 B2 | 3/2010 | Levine et al. |
| 7,682,330 B2 | 3/2010 | Meade et al. |
| 7,695,446 B2 | 4/2010 | Levine et al. |
| 7,758,535 B2 | 7/2010 | Levine et al. |
| 7,766,861 B2 | 8/2010 | Levine et al. |
| 7,766,973 B2 | 8/2010 | Levine et al. |
| 7,794,447 B2 | 9/2010 | Dann et al. |
| 7,806,870 B2 | 10/2010 | Mastri et al. |
| 7,815,591 B2 | 10/2010 | Levine et al. |
| 7,819,836 B2 | 10/2010 | Levine et al. |
| 7,824,368 B2 | 11/2010 | Clem et al. |
| 7,833,156 B2 | 11/2010 | Williams et al. |
| 7,833,202 B2 | 11/2010 | Suzuki |
| 7,837,643 B2 | 11/2010 | Levine et al. |
| 7,935,073 B2 | 5/2011 | Levine et al. |
| 7,976,488 B2 | 7/2011 | Levine et al. |
| 7,981,163 B2 | 7/2011 | Meade et al. |
| 8,057,420 B2 | 11/2011 | Meade et al. |
| 8,096,966 B2 | 1/2012 | Levine et al. |
| 8,097,000 B2 | 1/2012 | Albrecht |
| 8,109,910 B2 | 2/2012 | Zastawny et al. |
| 8,109,943 B2 | 2/2012 | Boraiah et al. |
| 8,137,301 B2 | 3/2012 | Levine et al. |
| 8,147,454 B2 | 4/2012 | Watanabe et al. |
| 8,147,561 B2 | 4/2012 | Binmoeller |
| 8,162,871 B2 | 4/2012 | Levine et al. |
| 8,182,459 B2 | 5/2012 | Dann et al. |
| 8,206,456 B2 | 6/2012 | Stack et al. |
| 8,211,186 B2 | 7/2012 | Belhe et al. |
| 8,246,617 B2 | 8/2012 | Welt et al. |
| 8,303,669 B2 | 11/2012 | Meade et al. |
| 8,430,811 B2 | 4/2013 | Hess et al. |
| 2002/0042607 A1 | 4/2002 | Palmer et al. |
| 2002/0055757 A1 | 5/2002 | Torre et al. |
| 2003/0097099 A1 | 5/2003 | Quinn |
| 2003/0158569 A1 | 8/2003 | Wazne |
| 2003/0225393 A1 | 12/2003 | McMichael et al. |
| 2004/0059289 A1 | 3/2004 | Garza |
| 2005/0240279 A1 | 10/2005 | Kagan et al. |
| 2005/0267415 A1 | 12/2005 | Jacques |
| 2006/0030872 A1 | 2/2006 | Culbert et al. |
| 2007/0123840 A1 | 5/2007 | Cox |
| 2007/0156165 A1 | 7/2007 | Chang et al. |
| 2007/0225728 A1 | 9/2007 | Stefanchik et al. |
| 2007/0255257 A1 | 11/2007 | Willis et al. |
| 2008/0249474 A1 | 10/2008 | Baker |
| 2009/0204067 A1 | 8/2009 | Abu-Halawa |
| 2009/0299486 A1 | 12/2009 | Shohat et al. |
| 2010/0081875 A1 | 4/2010 | Fowler et al. |
| 2010/0081883 A1 | 4/2010 | Murray et al. |
| 2010/0152764 A1 | 6/2010 | Merkle |
| 2010/0249822 A1 | 9/2010 | Nihalani |
| 2010/0280368 A1 | 11/2010 | Can et al. |
| 2010/0312047 A1 | 12/2010 | Forsell |
| 2010/0324375 A1 | 12/2010 | Piskun |
| 2010/0331756 A1 | 12/2010 | Meade et al. |
| 2011/0046537 A1 | 2/2011 | Errico et al. |
| 2011/0082442 A1 | 4/2011 | Solovay et al. |
| 2011/0106273 A1 | 5/2011 | Belhe et al. |
| 2011/0160539 A1 | 6/2011 | Robertson |
| 2011/0245751 A1 | 10/2011 | Hoffmann |
| 2011/0257580 A1 | 10/2011 | Meade et al. |
| 2011/0276091 A1 | 11/2011 | Melanson et al. |
| 2011/0301523 A1 | 12/2011 | Levine et al. |
| 2012/0029413 A1 | 2/2012 | Meade et al. |
| 2012/0078174 A1 | 3/2012 | Tai et al. |
| 2012/0095495 A1 | 4/2012 | Babkes et al. |
| 2012/0116362 A1 | 5/2012 | Kieturakis |
| 2012/0132212 A1 | 5/2012 | Nishtala |
| 2012/0184967 A1 | 7/2012 | Levine et al. |
| 2012/0203271 A1 | 8/2012 | Larkin et al. |
| 2012/0215152 A1 | 8/2012 | Levine et al. |
| 2012/0232339 A1 | 11/2012 | Csiky |
| 2012/0323081 A1 | 12/2012 | Son |
| 2013/0012862 A1 | 1/2013 | Meade et al. |
| 2013/0041231 A1 | 2/2013 | Bonadio et al. |
| 2013/0041372 A1 | 2/2013 | Welt et al. |
| 2013/0060091 A1 | 3/2013 | Azarbarzin et al. |
| 2013/0066304 A1 | 3/2013 | Belson et al. |
| 2013/0102876 A1 | 4/2013 | Limon et al. |
| 2013/0211196 A1 | 8/2013 | Belson et al. |
| 2014/0276338 A1 | 9/2014 | Pattison et al. |
| 2015/0038794 A1 | 2/2015 | Pattison et al. |

OTHER PUBLICATIONS

International Search Report and Written Opinion of the International Searching Authority Corresponding to International Application No. PCT/US2014/049639, dated Nov. 12, 2014.

International Search Report and Written Opinion of the International Searching Authority Corresponding to International Application No. PCT/US14/67689, dated Mar. 30, 2015.

International Search Report and Written Opinion of the International Searching Authority Corresponding to International Application No. PCT/US14/67697, dated Mar. 30, 2015.

ANCHORABLE SIZE-VARYING GASTRIC BALLOONS FOR WEIGHT LOSS

CROSS-REFERENCE TO RELATED APPLICATIONS

This application is a continuation-in-part of U.S. patent application Ser. No. 14/216,666 and PCT App. No. PCT/US2014/030625 each filed Mar. 17, 2014, each of which claims benefit of U.S. Provisional Application Nos. 61/790,709 filed Mar. 15, 2013 and 61/862,463 filed Aug. 5, 2013. Each of those applications is specifically incorporated by reference to the extent not inconsistent herewith.

BACKGROUND OF INVENTION

Provided herein are systems and methods related to obesity treatment and weight loss by a gastric restriction device, and that is implemented at least in part by transabdominal access to the gastric environment. The gastric restriction device corresponds to a size-varying gastric balloon that can be inflated to a deployed volume that occupies a significant fraction of the stomach volume and that is reliably anchored so as to prevent unwanted balloon migration.

In recent years obesity and related disorders, such as diabetes and atherosclerotic cardiovascular disease, have increased substantially. When compliance with diet, exercise and behavioral therapy fail to achieve weight loss, pharmacotherapy may be instituted. However, pharmacotherapy has had only modest success and may be discontinued if a patient experiences unpleasant side-effects. Long term safety of pharmaceutical use for treatment of obesity is uncertain, and patients generally regain lost weight when the therapy is discontinued. A variety of surgical treatments have recently become available for obesity, but typically as a last resort. Those surgical treatments have the advantage of more rapid initial weight loss and remission of diabetes mellitus than other non-invasive therapies. However, surgery is expensive, subject to risks of morbidity and mortality, and its efficacy may be reduced by patient noncompliance with post-surgical dietary restrictions. If patients fail to limit food intake, their bodies may undergo compensatory anatomical changes that partially overcome the effects of surgery. The most invasive surgical procedures tend to achieve the greatest long term percent change in weight, but also tend to be the most costly, require longer periods of recuperation and careful long term management of nutrients to avoid malnutrition.

Although there have been various attempts to treat obesity by minimally invasive procedures, those attempts still suffer from significant disadvantages including one or more of being relatively complex, difficult to modify or remove, result in permanent anatomical changes, or undergo efficacy degradation with time. The systems and related methods provided herein address these limitations in that the gastric-occupying devices are robust and long-lasting, while being easily inserted, positioned, manipulated and removed from a patient using a minimally invasive procedure.

SUMMARY OF THE INVENTION

A common problem with gastric balloons that are inflated to function as a gastric restriction device is that they can be difficult to control and maintain in an optimum position within the stomach. During use and over extended periods of time, the balloons tend to migrate and may increase the risk of malfunction, gastric obstruction or the like, and patient discomfort requiring active intervention and potentially balloon removal. Those drawbacks are a reflection of the difficulty in reliably anchoring the balloon to the stomach wall. One reason for this difficulty is that it is a challenge to handle and manipulate the balloon within the stomach lumen and reliably anchor the balloon to the stomach in a manner that does not adversely impact balloon function and the gastric environment.

Endoscopic procedures are limited in that the devices must be able to be inserted through the esophagus without causing undue irritation. This, therefore, inherently constrains the number and size of devices that can employed. Furthermore, it can be difficult to reliably control and position multiple endoscopes to specific locations. For these reasons, endoscopic procedures tend to be relatively simple with one endoscope and confined to the upper GI tract, generally the esophagus, stomach and duodenum so as to avoid increasing risk of complications.

Because of the inherent limitations of endoscopic procedures, laparoscopic procedures are also used for introduction of a medical instrument through the abdominal wall, thereby accessing the body's organs in an extra-luminal manner. In contrast to an endoscopic procedure where an instrument is introduced through the mouth, laparoscopy requires an opening be made through the abdominal wall for medical instrument access to the inside of the patient, such as the intraperitoneal space. This is typically achieved by using a trocar or other instrument having a sharp distal tip and a passage to provide a working passage for a medical instrument. Those trocars, however, suffer from inherent disadvantages and associated risks. First, the peritoneal membrane must be actively punctured from outside the patient to provide instrument access. This can result in increased risk of infection or other complications. Second, it can be difficult to reliably secure the trocar or other cannula-type element, including for extended periods of time with attendant movements on the trocar from instrument use during the surgical procedure. Lack of a safe, stable, and reliable working channel that traverses the abdominal wall can lead to unwanted complications. Furthermore, current technology requires that if a laparoscopic physician wishes to place a trocar into the gastric lumen via standard laparoscopic technique, they must make multiple abdominal incisions which will allow them to grasp the external wall of the stomach and then fix it to the abdominal wall by multiple suture/staple or other fixation methods. Once the stomach has been fixed in a safe and stable manner, the physician must make an external full thickness incision through the gastric wall and then externally place a surgical trocar that can be used for both passage and manipulation of laparoscopic instruments into the gastric lumen. The trocar must be air-tight to allow air insufflation of the stomach for both internal vision as well as manipulation of instruments. Trocars usually have internal air-tight seals for passage of instruments. The surgeon, however, must ensure an air-tight seal around the external aspect of the trocar to prevent air leakage on an external surface where the trocar contacts the gastric wall. This procedure is complex, with an attendant risk to establish intra-gastric access via laparoscopic surgery, and reflects the inherent difficulty in trocar insertion into a non-solid organ, such as a stomach. The problem of gastric lumen access for balloon manipulation and handling is addressed herein by specially configured trans-abdominal gastric systems having a cannula that provides a reliable and robust working channel to the gastric lumen. The working channel is easily achieved without any of the above-reference drawbacks. The working channel, or multiple working channels as desired, provides the ability to reliably and readily triangulate medical instruments to for superior control within the gastric lumen. In combination with a size-varying gastric balloon and attendant balloon anchors, precise and reliable balloon placement within the gastric lumen is achieved, in a non-permanent and non-surgical manner. For example, the balloon may be anchored to the gastric wall via one or more balloon anchors. This avoids direct suturing or stapling of the balloon to the gastric wall. If the balloon is to be removed from the patient, the anchors are simply released from the gastric wall, thereby avoiding the complications associated with cutting of sutures or removal of staples which directly attach the balloon to the gastric wall. Accordingly, the systems and methods provided herein avoid direct connections between the balloon to the gastric wall without sacrifice of reliable and long-term balloon positioning that minimizes the risk of gastric obstruction.

Provided are systems and related methods for obesity treatment. In particular, size-varying balloons positioned in the stomach lumen are inflated so as to occupy a substantial fraction of the stomach lumen. The balloons are configured to avoid unwanted migration during use by the use of specially configured anchors and attendant balloon and tissue manipulation through a transabdominal gastric cannula. In addition, the cannula may be used to deliver a fluid (e.g., liquid or air) from a location outside the patient to inside the balloon to expand its volume, such as via a fluid conduit positioned through the cannula lumen. Alternatively, a fluid port may be endoscopically accessed for introduction/removal of fluid to control balloon volume and, therefore, the fraction of the stomach lumen occupied by the balloon. The balloon itself may be specially shaped to mimic sleeve gastrectomy without permanent surgical resection. In fact, the systems described herein are readily controllable and removable, thereby avoiding adverse impacts should a subsequent surgical procedure arise.

Specific advantages of the systems and methods of the present invention include, adjustable balloon size permits the ability to tailor the procedure to the individual patient. In addition, the unique shape of certain balloons that mimic sleeve gastrectomy achieves the benefit of surgical sleeve gastrectomy without the disadvantages associate with permanent surgical resection. The anchors of the present invention avoid more permanent type fastening means that are more difficult to reverse without impacting the ability to prevent balloon migration. The systems and procedures are less invasive and are not associated with a permanent anatomic change. Furthermore, general endotracheal anesthesia (GETA) is avoided, and there is decreased mortality and risk of malnutrition.

In an embodiment, the invention is a gastric balloon system for treatment of obesity in a patient. The system may be broadly described in terms of certain general components. One important component is a size-varying gastric balloon, whose function is to provide a feeling of fullness or satiety to a patient, thereby decreasing appetite. Particularly useful size-varying gastric balloons are those having an annulus and elements to avoid distal migration after deployment in the stomach lumen, such as one or more gastric anchor configured to connect the balloon to the stomach wall, where the anchors still, however, permit constrained movement. Another important component, in certain aspects, is a transabdominal gastric cannula, also referred herein as a transabdominal gastric system. Examples of various such gastric cannula systems are provided herein, and also in, for example, U.S. patent application Ser. No. 14/451,108 titled "Transabdominal Gastric Surgery System and Method" filed Aug. 4, 2014, and Ser. No. 14/554,337 titled "Transabdominal Gastric Device and Method" filed Nov. 26, 2014 which are specifically incorporated by reference herein for any of the systems disclosed therein for use with any of the balloons provided herein. The transabdominal gastric cannula provides certain functions, including as a reliable anchor for one or more of balloon insertion, manipulation, inflation, deflation and/or attachment. Furthermore, additional transabdominal gastric cannula may be used to provide added flexibility with respect to balloon handling. Finally, a malabsorptive sleeve may be used in combination with a gastric balloon and/or a transabdominal gastric cannula. Each of those three components is independently selectable and compatible with the other components, so that any balloon may be used with any transabdominal gastric cannula and/or with any malabsorption sleeve.

In an embodiment the gastric balloon system for treatment of obesity comprises a transabdominal gastric cannula for gastric balloon insertion and/or manipulation in a stomach lumen and a gastric balloon. The cannula is a passage that, during use, provides access to the gastric environment by a working channel. Accordingly, the working channel is an important aspect in that improved balloon manipulation, such as for balloon anchoring to a gastric wall is achieved. The gastric cannula may comprise an outer end, an inner end, and a central portion having an outer-facing surface that extends between the inner end and the outer end, and an inner-facing surface that defines a lumen configured to receive a portion of a medical instrument that traverses between the outer end and the inner end. An internal anchor is connected to the inner end and has a surface shape configured to secure the system against an interior surface of a gastric wall or peritoneal surface. In this aspect, connected is used broadly to include a single piece of material having a portion defined as an internal anchor from which a cannula extends. Alternatively, the connection may refer to two separate pieces, the cannula and internal anchor, which are permanently or removably connected. An external anchor is removably and translationally connected to the cannula outer-facing surface and has a surface shape configured to secure the system against a skin surface. an outer end. A size-varying gastric balloon is configured for delivery or insertion to a stomach lumen through the transabdominal gastric cannula or endoscopically via the patient's esophagus. The gastric balloon may comprise a gastric balloon surface; an internal volume defined by the gastric balloon surface; a gastric balloon anchor connected to the gastric balloon surface configured to reliably position and anchor the size-varying gastric balloon in a gastric environment. For control of the internal volume of the size-varying gastric balloon, a fluid conduit or port may be fluidically connected thereto. The fluid conduit or port may have a first fluid end and a second fluid end, wherein the first fluid end is fluidically connected to the size-varying gastric balloon internal volume and the second fluid end is positioned externally or internally relative to the patient for connection to a fluid source. The fluid conduit is configured to introduce a fluid to gastric balloon internal volume to increase the internal volume to a deployed internal volume and provide a gastric balloon deployed configuration. The second end of the fluid conduit may be positioned outside the patient for a convenient access point for a fluid source or sink for balloon inflation or deflation, respectively, or via a subcutaneous port. Alternatively, the second end of the fluid conduit may be positioned internally and a fluid source introduced endoscopically, such as via a needle and port through the balloon wall. The fluid, as desired, may be a gas, a liquid, or a viscoelastic material that flows under an applied force, such as a gel.

An important aspect of the instant invention is the ability to precisely position and maintain the gastric balloon in the stomach lumen. This reduces risk of balloon migration and attendant gastric obstruction and patient discomfort. In an aspect, the gastric balloon anchor is connected to the transabdominal gastric cannula, thereby tethering the gastric balloon in a desired position within the stomach lumen. Alternatively, or in addition thereto, the balloon is anchored independently to the stomach wall by one or more anchors connected to the balloon outer surface.

Accordingly, in another aspect the invention is a gastric balloon anchor, such as an anchor configured for use with any type of size-varying gastric balloon. The gastric balloon anchor may be used to retro-fit a conventional size-varying gastric balloon, so that any balloon known in the art may be used with the gastric cannulas provided herein for reliable anchoring, thereby facilitating long-term balloon insertion without unwanted side effects. The anchor may be further described as providing constrained movement or motion. "Constrained motion" refers to the anchor that provides some degree of movement relative to the balloon and the gastric wall. In an aspect, constrained motion refers to an at least partial rotational motion movement in the anchor. Such constrained motion can accommodate various forces and motions in the stomach and movement of the stomach wall. This provides a functional benefit of prolonging balloon lifetime and avoiding patient discomfort commonly associated with conventional gastric balloons.

In an aspect, the anchor comprises an anchor mount having an opening for receiving one or more pre-sutures or preclosure sutures. A fastener has a first end that is connected to the gastric balloon surface and a second end connected to the anchor mount. The connection may be a movable connection, so that the anchor mount can move relative to the fastener second end to the sutures or corresponding stomach wall after suture closure.

The anchor mount may be a ring that receives a second end that is a fastener coupling, such as a fastener ring. In this manner, the two interlocking rings may move relative to each other, but in a manner that is constrained, thereby ensuring unwanted balloon migration is avoided while also avoiding undesired effects associated with a more rigid anchor connection.

The fastener first end may be embedded in the size-varying gastric balloon wall, such as during balloon manufacture. Alternatively, an already constructed size-varying gastric balloon may be retrofitted with the anchor, such as by affixing the fastener first end to the balloon outer surface, such as by an adhesive.

In an aspect, any of the gastric balloon systems further comprise any of the gastric balloon anchors provided herein.

In an aspect, the fluid conduit is connected to an anterior portion of the size-varying gastric balloon and traverses the cannula lumen. In this aspect, therefore, the fluid cannula may serve the dual functions of being an anchor (such via the transabdominal gastric cannula) and to provide balloon inflatability/deflatability.

In another embodiment, the fluid conduit is connected to a cephalad portion of the size-varying gastric balloon and traverses a patient's esophagus. "Cephalad portion" refers to the portion of the balloon that is oriented toward the top of the stomach and accessible by the esophagus.

Any of the systems and methods describe may have a second gastric cannula, such as to provide independent access to a medical device, implant, or the like. In an aspect, the system further comprises a second fluid conduit and a second transabdominal gastric cannula through which each fluid conduit independently traverses, each first fluid conduit end connected to an anterior portion of the size-varying gastric balloon with the connections separated from each other by a fluid conduit separation distance that is greater than or equal to 15 cm to provide a two inflation ports, deflation and inflation ports, or two deflation ports. Use of two gastric cannulas provides the ability of instrument triangulation and further improved control and manipulation of the balloon, anchor and stomach wall tissue. In this manner, fundamentally improved balloon anchoring is achieved.

The configuration of the transabdominal gastric cannula provides the ability for reliable removal, so that after activation of a gastric balloon deployed configuration, the transabdominal gastric cannula may be removed from the patient, including providing reliable balloon anchoring and tissue defect closure in a single, convenient and reliable step. Alternatively, the system may be configured for long-term use of the transabdominal gastric cannula. For example, for a transabdominal gastric cannula having a low profile, and after deployment to the gastric balloon deployed configuration, the transabdominal gastric cannula may be retained in the patient.

The fluid conduit may be configured to remove a fluid from the internal volume to decrease the gastric balloon internal volume, such as from a deployed state to a relaxed state, such as ahead of balloon removal or for a controlled decrease in the internal volume, such as by at least 10%, 20%, 50% or 90%.

The fluid conduit may be connected to a fluid source external to the patient for introducing a fluid to the internal volume to control the size-varying gastric balloon shape and size. The fluid may be a gas, a liquid or a gel. For a balloon having air, the gas source may simply be the surrounding environment. For a liquid the liquid may be water or saline, for example.

Any of the systems provided herein may have a fluid conduit connected to the transabdominal gastric cannula. Alternatively or in addition thereto, a fluid conduit that is positioned within the gastric lumen may be accessed by an endoscopically introduced fluid source and/or a laparoscopically introduced fluid source through the gastric cannula working channel.

In an embodiment, provided is a size-varying gastric balloon having an annulus in a deployed configuration configured to align in the stomach to pass food and liquid in a direction from an esophageal exit toward a pyloric sphincter. The annulus facilitates movement of materials naturally through the stomach and minimizes risk of a gastric obstruction, without unduly sacrificing the feeling of fullness by the patient. This further enhances deployed balloon stability, longevity, and decrease in complications associated with other balloons. Furthermore, the transabdominal gastric cannula provides an important functional benefit of enhanced handling in the stomach lumen and attendant improvement in balloon anchoring and positioning.

The annulus may have an average diameter that is greater than or equal to 0.5 cm and less than or equal to 5 cm and a deployed volume that occupies at least 75% of the stomach lumen. "Average diameter" may be determined in any number of ways, and is a reflection that given the flexible nature of the balloon and curved nature of the annulus, the diameter may not be constant. For example, a diameter may be obtained for a select number of points along the annulus, and an attendant average calculated from those points. The annulus may be further described in terms of a length, such as a length that is greater than or equal to 5 cm and less than or equal to 50 cm.

The annulus may be a straight line passage or may be curved. During use the annulus has an entry end configured to be aligned and separated from a patient's esophageal exit; and an exit end configured to be aligned and separated from a patient's pyloric sphincter. In this context, "alignment" refers to the ability of a material to pass from the esophagus into the annulus inlet or from out of the annulus exit and out the stomach via the pyloric sphincter, without substantial risk of blockage. The outermost edge of the balloon may be separated from the inner surface of the gastric balloon, but at a sufficiently low value to minimize or avoid food being trapped between the balloon and the stomach wall.

The gastric balloon system of the instant invention may be described as having, during use, at least 75% of the stomach lumen occupied by a deployed balloon and less than 25% of the stomach lumen unoccupied by the deployed balloon, wherein at least 60% of the unoccupied stomach lumen volume is in a distal stomach portion adjacent to a pyloric sphincter to avoid gastric obstruction; and less than 20% of the unoccupied stomach lumen is in a proximal stomach portion adjacent to an esophageal sphincter. In another aspect, the annulus has an entry end that is separated from the esophageal exit by an esophageal distance that is between 2 cm and 5 cm; and said annulus exit end is separated from the pyloric sphincter by a pyloric distance that is between 2 cm and 5 cm. In this manner, the likelihood of a gastric obstruction is minimized or avoided. The unique construction of the balloon and balloon anchors ensures that the balloon does not migrate in a distal direction during use, thereby maintaining the large unoccupied distal stomach portion relative to the proximal stomach portion.

In an embodiment, during use the entry end and the exit end are substantially fixably positioned within a gastric environment by a plurality of gastric balloon anchors. In this context, "substantially fixably positioned" refers to minimal migration of the ends in a distal direction, such as less than 1 cm or less than 5 mm over the course of the treatment. The systems and methods are designed for a treatment course of greater than 1 month, greater than 3 months, greater than 6 months, or between about 1 month and three years. The specially-configured anchors that connect the balloon to the gastric wall and accessed by the working channel(s) provides some movement, described herein as constrained motion that allows much longer balloon implant function compared to conventional systems.

The gastric balloon anchors may each comprise a first end operably connected to the gastric balloon surface and a second end configured to connect to a gastric wall during use. Alternatively, the anchor can connect to the transabdominal gastric cannula, such as via a tether-type mechanism. This aspect is particularly useful for those applications where the gastric cannula remains in the patient long-term. Any of the gastric balloon anchors may have one end that is integrally inserted into the balloon wall. Alternatively, the end may be affixed to the outer-surface of the balloon, such as with an adhesive. In this manner, any conventional gastric balloon known in the art may be retro-fitted with an anchor for use with any of the systems or methods provided herein.

An example of another type of gastric balloon anchor is the fluid conduit connected to the internal volume that corresponds to a percutaneous catheter that passes through and is connected to the transabdominal gastric cannula.

Any of the systems and methods provided herein may further comprise an elongated sleeve configured for insertion into a portion of a patient's small intestine, the elongated sleeve having a lumen and a proximal end connected thereto, the proximal end configured for positioning at or adjacent to a pyloric sphincter and aligned with the gastric balloon annulus during use.

In an embodiment, the invention is a gastric balloon system for treatment of obesity comprising a size varying gastric balloon having: an outer-facing surface; an inner-facing surface, wherein the inner-facing surface defines an annulus in a deployed configuration, said annulus having an entry, an exit, an annulus length between the entry and exit that is greater than or equal to 5 cm and less than or equal to 50 cm; and an annulus diameter that is greater than or equal to 0.5 cm and less than or equal to 5 cm; an interior volume defined by the outer-facing surface and the inner-facing surface; a fluid port or cannula having a first end fluidically connected to the interior volume for controllably introducing a fluid to increase a volume of the size-varying gastric balloon. Such a balloon geometry advantageously avoids gastric obstruction and can optionally be used with any of a wide variety of transabdominal gastric cannula.

One example is a transabdominal gastric cannula having a lumen or working channel along which the percutaneous cannula traverses and that positionably secures the size-varying gastric balloon in a stomach lumen. The transabdominal gastric cannula may further comprise an internal anchor configured to secure said transabdominal gastric cannula to a gastric surface; and an external anchor configured to contact a skin surface. The internal and external anchors reliably anchor the transabdominal gastric cannula to the gastric surface during use. In an aspect, the fluid port may be a percutaneous cannula that traverses the working channel to provide the ability to inflate/deflate the gastric balloon in the stomach lumen.

As desired, a second transabdominal gastric cannula for introducing one or more instruments to the gastric environment may be used, such as an instrument to assist with balloon and anchor manipulation and/or insertion of a malabsorption sleeve in the small intestine.

The gastric balloon system may have one or more gastric balloon anchors, each having a first end connected to the outer facing balloon surface, and a second end configured to connect to a gastric surface. The anchors can be specially configured to provide constrained balloon motion and movement, thereby increasing balloon lifetime with attendant improved patient outcome with respect to weight loss without substantial side effects. In a gastric balloon deployed configuration, the gastric balloon and annulus each may be curved in a longitudinal direction with a substantially cylindrical outer shape to substantially align the longitudinal direction with a stomach lumen during use; and at least 75%, at least 80%, or at least 90% of the stomach lumen is occupied by the gastric balloon. One advantage of the size-varying balloon, is the ability to adjust balloon volume depending on individual patient needs or responsiveness.

Also provided are various methods for treating obesity by using any of the systems described herein. In an embodiment, the method of treating obesity in a patient is by inserting a size-varying gastric balloon in an undeployed configuration into a stomach lumen, wherein the size-varying gastric balloon optionally has an annulus; securing the size-varying gastric balloon to a stomach wall or a transabdominal gastric cannula, such as via one or more gastric anchors, wherein the optional annulus is positioned in a longitudinal orientation relative to the stomach lumen; and introducing a fluid to an internal volume of the size-varying gastric balloon to provide the size-varying gastric balloon in a deployed configuration that occupies at least 75% of the stomach lumen, wherein the annulus is substantially aligned with the esophageal and pyloric sphincters to reduce risk of a stomach blockage during use.

The deployed configuration may provide a balloon-pyloric sphincter open space volume that is greater than a balloon-esophageal sphincter open space volume throughout a treatment window. This aspect is important to minimize the risk of a gastric block and/or patient discomfort associated with food-material build-up in the pyloric sphincter region by ensuring sufficient and maintained separation between the balloon distal end and the pyloric sphincter.

In an aspect, the inserting step comprises inserting a transabdominal gastric surgical system through an abdominal wall by a retrograde introduction, the inserted transabdominal gastric surgical system having a cannula lumen with an inner end connected to an internal anchor and an outer end connected to an external anchor, with a patient's abdominal wall positioned therebetween. The gastric balloon introduced from outside the patient may be endoscopically introduced, or introduced via the working channel, along the cannula lumen, and into the stomach lumen. Optionally, the gastric balloon is anchored to the transabdominal gastric system, such as at the internal anchor with a tether and/or via a fluid conduit that is fluidically connected to balloon and traverses the cannula lumen and through an instrument port or that is connected to a pressure port.

A second transabdominal gastric surgical system may be inserted through the abdominal wall at a different location than the first through which the balloon is inserted. The introduced gastric balloon may be manipulated with a medical instrument that traverses the second transabdominal gastric surgical system. The manipulation may refer to placement of the balloon with a grasper and/or fastening of a balloon anchor to the gastric wall. Multiple working channels from multiple gastric cannula provide a convenient platform to triangulate instruments at a desired anchor point, including by visualization with an endoscope.

In an aspect, the securing step comprises attaching one or more gastric balloon anchors to a top portion and/or a sidewall portion of the stomach wall to prevent distal migration of the deployed balloon in a direction toward a pyloric sphincter. The sidewall attachments may comprise about three or four anchors circumferentially spaced and separated toward the proximal or top of the stomach to further minimize risk of distal migration.

In an embodiment, the introducing step comprises fluidically connecting a fluid cannula to the gastric balloon interior volume through a transabdominal wall of the patient such as via the cannula working channel, or through an endoscope, the fluid cannula having an outer end positioned outside the patient; and introducing a fluid to said gastric balloon internal volume via the fluid cannula outer end, thereby increasing the gastric balloon internal volume, including to the deployed state so as to occupy at least 75% of the stomach lumen.

The method may further comprise the step of introducing a malabsorption sleeve to at least a portion of a small intestine of the patient, wherein a malabsorption sleeve inlet is positioned at or adjacent to a pyloric sphincter and substantially aligned with an exit of the annulus.

In an aspect, the anchoring step further comprises placing one or more pre-sutures or preclosure sutures through an anchor mount opening, so that during tissue wall defect closure with the sutures during removal of the gastric cannula, the anchor is also secured to the gastric wall. Such a configuration allows fast and reliable wall closure and anchoring in a single step.

As part of the weight loss device to which the balloon is anchored, accessed, and/or inserted into the body, provided herein is a trans-abdominal gastric surgical system or, more generally, a transabdominal gastric cannula that provides access to a patient's abdominal cavity from outside the patient through the abdominal wall with a uniquely inserted, secured and removable cannula, including any of the systems described in U.S. patent application Ser. No. 14/451,108 filed Aug. 4, 2014, which is specifically incorporated by reference herein. The unique structure and implementation of the systems described herein provide a number of important functional benefits that increase the likelihood of a successful outcome and minimizes risk of an adverse event. First, the gastric cannula is readily and easily deployed, with a retrograde introduction from the oral-pharynx, esophagus, to the stomach lumen, and into the abdominal wall, with an internal anchor in contact with an inner-facing surface of the stomach wall by a simple pulling force on a guidewire connected to the system that passes through an incision in the abdominal wall. Once in place, the cannula portion is readily anchored through the use of opposed anchors, an internal anchor that is anchored to the gastric or peritoneal surface and an external anchor opposed to the internal anchor that is anchored to the skin surface. This results in an extremely reliable and robust positioning of the cannula, through which a surgeon can access internal regions of a patient, including a gastric balloon, anchors, and the lumen-facing portion of the stomach wall. Furthermore, a fluid conduit can be readily positioned through the lumen of the transabdominal gastric cannula to provide controlled inflation and/or deflation of the gastric balloon. Closure elements may be inserted at the start of the procedure, making system removal and incision closure simple, quick and reliable with an attendant decrease in scarring-related issues, tissue sensitivity, pain, infection and wound re-opening. In particular, the closure elements may be integrated with the anchor, so that upon tissue closure, balloon anchoring to the stomach wall is simultaneously achieved in a rapid, reliably and robust manner.

Optionally, the balloon is preconnected to the gastric cannula ahead of a retrograde introduction, such as to the internal anchor prior to gastric cannula introduction to the patient, so that after the gastric cannula is introduced the balloon is prepositioned in an undeployed state in the stomach lumen. Alternatively, the balloon is inserted into the stomach lumen after the gastric cannula is placed in the patient, such as via an endoscopic introduction through the esophagus or a laparoscopic introduction via the gastric cannula. The balloon may then be inflated from an undeployed to a deployed configuration by introduction of a fluid to the balloon lumen. The working channel(s) of one (or more than one) gastric cannula is an important aspect that facilitates precise and reliable balloon anchoring to the gastric wall, and attendant functional benefits.

The systems are compatible with a wide range of applications including related to the ability to manipulate tissues, manipulate and anchor implanted devices such as balloons and/or sleeves, provide internal sutures, and accommodate a variety of anastomotic devices. An application of interest herein, is weight loss via balloon inflation in the stomach lumen and the attendant medical instruments introduced through the gastric cannula, such as graspers and manipulators for balloon and/or sleeve positioning and anchoring.

Further advantages include the ability to maintain a desired spatial orientation during a surgical procedure as well as providing the ability to multitask via the introduction of a plurality of medical instruments that do not interfere with each other. If there is an adverse event during a surgical procedure, the systems herein allow for rapid management and mitigation, including any of a number of intraperitoneal complications such as a hemorrhage event, balloon failure, or the like. Other advantages include the ability to triangulate on a specific region of interest in either a one-cannula or two-cannula configuration. This is particularly useful for the balloon anchoring aspect, where it is otherwise impractical to manipulate the balloon, anchor and pre-sutures. Furthermore the systems provided herein are compatible with any generic endoscopic or laparoscopic instrument to provide a degree of control not previously possible. Such control is an important part of ensuring appropriate balloon positioning.

The minimally invasive and low complication incidence provided by the instant systems means unwanted physiological events are avoided along with attendant decrease in training efforts and costs, with both improved patient outcomes and decreased healthcare costs that are otherwise associated with failure to address obesity adequately. The simplicity and elegance of the systems ensure a rapid learning curve is achieved by a spectrum of caregivers.

In an embodiment, provided herein is a trans-abdominal gastric surgical system that can be used with any of the balloons provided herein.

In use, the transabdominal gastric system provides two opposed surfaces connected to and securing the cannula to the abdominal wall, with the internal anchor securing the system in a direction from the gastric environment to the abdominal wall, and a counter-directed force from the external anchor toward the abdominal wall.

The systems and related methods provided herein are a useful platform for a number of applications. Depending on the application of interest, the system accommodates a medical instrument that extends from outside the body to inside the body, via the working channel or cannula passage. Examples of medical instruments include, but are not limited to, laparoscopic and endoscopic instruments for minimally invasive surgery such as for tissue incision, removal, handling, illumination, surgery, suturing, stapling and the like.

In an embodiment, the internal anchor surface shape is adjustable, deployable, or both. Examples include an internal anchor selected from the group consisting of: a balloon; a hinged umbrella; and a flexible bumper. In a more basic implementation, the internal anchor surface does not substantially change shape, but instead is shaped and sized to permit endoscopic introduction from the mouth to the stomach while maintaining the ability to reliably secure the device against an internal-facing surface, such as the gastric wall or a peritoneal surface.

In an aspect, the internal anchor encircles the cannula inner end and is configured to secure the system to an interior surface of a gastric wall or an interior surface of a peritoneal cavity. In an embodiment, the internal anchor comprises a bumper and the bumper and the cannula are formed from a unitary material.

The bumper has a shape to provide reliable contact with a patient's inner-facing surface, including the stomach wall or a peritoneal cavity surface. For example, the curved outer surface may have a maximum diameter that is greater than or equal to 2 cm and less than or equal to 4 cm, a height that is greater than or equal to 0.5 cm and less than or equal to 2.5 cm, an open exit having a diameter that is less than or equal to 3.5 cm; and a hollow interior volume defined by said curved outer surface and through which a medical device can traverse. The hollow interior volume advantageously provides a well-defined space through which a medical device extends, thereby assisting with medical device control and positioning to enhance stability, while minimizing adverse effects on surrounding tissue during medical device insertion and removal and during an extended medical procedure.

Any of the systems provided herein may have an external anchor that comprises a disc having an inner-facing surface that defines a passage for receiving the cannula. In this aspect, the cannula and inner-facing surface may have a circular shape to provide a translational connection by a matched internal thread and external thread pair on facing surfaces of the disc inner-facing surface and the cannula outer-facing surface, wherein rotation of the disc relative to the cannula outer-facing surface translates the disc along at least a portion of the cannula outer-facing surface in a longitudinal direction along the cannula axis. Alternatively, the translational connection may comprise other connections, such as a friction-fit, clamp fit, or set screw fit.

In an aspect, the disc comprises a central body that defines the passage and a flange connected to the central body, the flange comprising a plurality of passages extending there through. The plurality of passages may be arranged in a circumferential offset pattern relative to a central body having a substantially circular shape. Adjacent passages may be separated by a separation distance that is greater than 1 mm and less than 4 mm and have alternating separation distances from the central body corresponding to a minimum separation distance and a maximum separation distance. For example, the minimum separation distance may be less than about 7 mm and the maximum separation distance greater than about 7 mm.

The flange may have an outer edge that comprises a plurality of straight edges, such as an octagon shape and corresponding number of passages. For example, the plurality of passages may number eight, with four corner-positioned passages and four side-positioned passages. Adjacent corners may be separated by an individual side-positioned passage, with the corner-positioned passages separated from the central body by the maximum separation distance and the side-positioned passage separated from the central body by the minimum separation distance. In an aspect, each of the plurality of passages is positioned adjacent to a corner region of the octagon shape flange outer edge. Each of the passages may be positioned within about 1 cm from the edge of the flange. In an aspect, each of the edges that define the flange outer edge has equal lengths. For an octagon embodiment, the edges may have a length that is between about 1 cm and 2 cm and accordingly spaced from an outermost edge of the central body of between about 0.5 cm and 1.5 cm. The maximum length of the disk may be between about 2 cm and 5 cm.

Any of the systems provided herein may further comprise a plurality of suture threads, wherein each individual suture thread traverses a pair of opposed passages, and may loop around an outermost portion of the internal anchor, without adversely impacting any of the one or more medical devices extending there through. For example, the suture threads may be positioned at the start of a procedure, the procedure performed, medical devices removed, and the suture threads pulled to remove the system from the patient and to reliably close an incision, as explained hereinbelow. Preferably, the presutures are operably connected to the gastric balloon anchor, as described herein, so that defect closure also results in balloon anchoring to the gastric surface.

Any of the systems provided herein may further comprise a cap removably connected to the cannula outer end. Such a cap is useful to providing an air-tight passage for introduction of medical instruments through the cannula from outside a patient so that a distal end of the medical instrument is provided inside the patient and extending past the internal anchor. For balloon volume control via inflation/deflation, a useful type of medical instrument is a fluid conduit fluidically connected to the balloon that introduces and/or removes a material from the balloon lumen, thereby controlling balloon volume The cap may comprise one or more instrument ports configured for introducing one or more medical instruments to the cannula lumen and out of the inner end and into a patient when the system is anchored to a gastric wall or a peritoneal surface by the internal anchor and a skin surface by the external anchor.

The cap may comprise a plurality of instrument ports formed from a memory sealant, each instrument port having an independently selected size and introduction angle. The memory sealant may be a shape memory polymer. The memory sealant may be formed from a single layer or a multilayer. In such a manner, upon removal of the medical instrument, the memory sealant may form an airtight seal between the external and internal side of the sealant.

In an aspect, any of the systems may further comprise a pressure port operably connected to the cap for measuring or controlling pressure at the cannula inner end or in a balloon that is fluidically connected to the pressure port. In this manner, the balloon lumen may be pressurized to a desired pressure, such as to achieve a desired shape and volume, including to occupy a substantial fraction of the stomach lumen, such as greater than 75% in a desired position.

In an aspect, any of the systems may further comprise a stopcock connected to the cap for providing controlled access to the cannula lumen or a fluid conduit connected thereto.

Any of the systems provided herein may also be configured for introduction or insertion into the gastric lumen, such as by a retrograde introduction to the stomach from the esophagus. Accordingly, the system may have an external anchor removed configuration for the external anchor removed from the cannula. In this aspect, the system may further comprise an introducer removably connected to the cannula outer end in the external anchor removed configuration. Such external anchor removal may ready the system for insertion into a patient.

In this aspect, the introducer may comprise a receiving opening that removably receives the cannula outer end and at least a portion of said cannula central portion. The connection may be equivalent to the connection employed with the external anchor-cannula connection.

In an embodiment, the introducer comprises a distal end; a proximal end through which the receiving opening traverses; a tapered central portion extending between the distal end and the proximal end; a capture element connected to the distal end; and wherein the tapered central portion is configured for introducing the system to a patient by retrograde introduction past a patient's oropharynx by pulling a guidewire connected to the capture element in a direction away from the introducer connected to the system.

In an embodiment, the introducer and cannula have a flexibility or bending moment selected so that the introducer is capable of deforming to follow contours of a patient oral-pharynx and esophagus during insertion in a patient.

Once the introducer is pulled through the guidewire insertion region, the introducer is removed to provide a system having an introducer removed configuration. The system in an introducer removed configuration is then ready to receive an external anchor that is connected to the cannula outer surface in an external anchor deployed configuration.

In another embodiment, the invention is an insertable trans-abdominal gastric surgical system comprising an introducer having a receiving passage and an outer tapered surface; a cannula having an outer end removably connected to the introducer receiving passage; an inner end; and a central portion having an outer-facing surface that extends between the outer end and the inner end and an inner-facing surface that defines a lumen configured to receive a portion of a medical instrument that traverses between the outer end and the inner end. An internal anchor is connected to the inner end and has a surface shape configured to secure the system against an interior surface of a gastric wall or peritoneal surface and to optionally provide a tether point for any of the gastric balloons described herein to facilitate balloon positioning and placement. The introducer, cannula and internal anchor are configured for insertion to a patient's gastric lumen by retrograde introduction past a patient's oropharynx, along an esophagus, and into the stomach lumen.

Any of the systems provided herein may have an introducer that comprises a distal end; a proximal end through which the receiving passage traverses, wherein the receiving passage has an at least partially threaded inner-facing surface to rotationally and removably engage an at least partially threaded cannula outer facing surface.

Any of the systems provided herein may have an introducer further comprising a capture element connected to the distal end configured to connect to a guidewire to facilitate guided insertion in a direction through a patient's oropharynx, esophagus, stomach and abdominal wall, such as by a pulling action of the guidewire that is connected to the capture element away from the system. In this manner, the capture element then transmits the pulling action to the rest of the system, thereby moving the entire system.

In an aspect, the invention may be further described in terms of the outer tapered surface having: an angle of incidence at the distal end that is greater than or equal to 5° and less than or equal to 20°; a total length that is greater than or equal to 2 cm and less than or equal to 15 cm; a tapered portion extending from the distal end and a substantially untapered portion extending between the proximal end and the tapered portion, having a tapered portion longitudinal length to untapered portion longitudinal length ratio ($L_T/L_U$) that is greater than or equal to 1 and less than or equal to 5; and wherein the introducer has a flexibility selected so that said introducer is capable of deforming to follow contours of a patient's oral-pharynx and esophagus during insertion into a patient.

In an aspect, the cannula portion of the system may be further described in terms of certain dimensions, such as length and diameter. For example, the cannula length may be between 4 cm and 30 cm, and any sub-ranges thereof, such as between 6 cm and 10 cm. The cannula diameter may be selected from a range of between 5 mm and 70 mm, including a diameter that is greater than or equal to 5 mm and less than or equal to 20 mm, and any sub-ranges thereof. The introducer diameter may be accordingly sized to match the cannula diameter, such as a diameter of between 5 mm and 70 mm, or between 5 mm and 20 mm, and any sub-ranges thereof.

The introducer and/or cannula may be made from a material having a desired durometer, rigidity and flexibility, such as medical grade silicone, polyvinyl chloride (PVC), plastic, rubber, or other material known in the art of medical devices and implants.

Also provided are various methods related to any of the systems described herein. In an embodiment, provided is a method of inserting a trans-abdominal gastric surgical system in a patient by inserting a guidewire through an abdominal wall insertion and into a stomach lumen; guiding a portion of the inserted guidewire out of the stomach lumen, through an esophagus and mouth to provide an accessible portion of the guidewire; connecting a capture element of an introducer trans-abdominal gastric surgical system assembly to the accessible portion of the guidewire; pulling the guidewire connected to the capture element of the introducer trans-abdominal gastric surgical assembly in a direction away from the patient so the assembly is introduced into the stomach lumen; advancing the introducer portion of the assembly out of the stomach through the abdominal wall incision so that an internal anchor of the trans-abdominal gastric surgical system contacts an inner-facing surface of the stomach; removing the introducer from the assembly to reveal an exposed end of trans-abdominal gastric surgical system; removing the guidewire; connecting an external anchor to the exposed end of the trans-abdominal gastric surgical system; and moving the external anchor in a direction toward a skin surface of the patient to reliably secure the trans-abdominal gastric surgical system to the patient. In this manner, the trans-abdominal gastric surgical system is inserted and reliably secured to the abdominal wall of the patient.

In an aspect, the method further comprises the step of attaching a cap to the exposed end of the inserted trans-abdominal gastric surgical system. Alternatively, the system may be configured to have a self-contained cap over which the introducer extends, so that upon removal of the introducer, the cap is revealed.

The method is further useful for a variety of surgical procedures, including a procedure on a human or a non-human animal. For example, the method may further comprise the step of introducing one or more than one surgical instruments through the trans-abdominal gastric surgical system for use in a procedure selected from the group consisting of: weight loss via gastric balloon insertion in the gastric lumen; malabsorption sleeve in the upper GI tract or small intestine region; instrument triangulation; accessing a stomach lumen; accessing a retroperitoneal space; manipulating tissue; closing an incision; a gastric surgery; a gall bladder surgery; single or simultaneous access to an upper GI tract and small intestinal lumen; access of an intra-peritoneal space; and access of an extra-peritoneal space and associated organs, or any combination thereof.

In an aspect, any of the methods further comprise the step of removing the trans-abdominal gastric surgical system after procedure completion in a reliable, simple and robust manner that minimizes post-operative discomfort or complications, and that simultaneously anchors the balloon to the stomach wall. The removal may comprise inserting at a start of or before the procedure a plurality of sutures by: introducing a cannulated-introducer needle through a first passage in the external anchor and through a first underlying tissue region comprising an abdominal and gastric wall and into a gastric environment, either for a single-layer closure or in a repeated manner for multiple-layer closure; introducing a suture grasper through a second passage in the external anchor and through a second underlying tissue region comprising the abdominal and gastric wall and into the gastric environment, wherein the second passage is opposibly positioned relative to the first passage; placing a suture thread proximal portion through the cannulated-introducer needle; guiding a suture thread distal portion around and away from the outer-facing surface of the internal anchor to ensure there is no interference by the thread on movement and use of a medical instrument passing therethrough and guiding the suture thread through the anchor mount opening, wherein the suture thread distal portion longitudinally extends from the suture thread proximal portion; grasping at least a portion of the suture thread distal portion with the suture grasper; pulling the suture grasper and suture thread distal portion out of the gastric environment. through the anchor mount opening, and through the underlying abdominal and gastric wall and the external anchor second passage wherein the suture thread portion in the body is positioned around or beyond said internal anchor to avoid interference with an instrument introduced through a working channel formed by the trans-abdominal gastric surgical system, and securing the suture ends outside the body to ensure the suture thread ends are not pulled back into the patient, such as by clamps that lay externally to the patient, thereby providing a reliable pre-closure suture; repeating the above steps with a second suture thread positioned through a third external anchor passage, fourth external anchor passage, and corresponding third and fourth underlying tissue regions comprising the abdominal and gastric wall; optionally, the steps are repeated with a third suture thread and fifth and sixth external anchor passages, as desired and depending on the number of available external anchor passages. The cannulated-introducer needle and the suture grasper are removed to reveal matched pairs of suture thread proximal and distal portions that extend out past the external anchor outside the patient skin surface and that each traverse through the anchor mount opening; the external anchor is loosened or optionally removed from the exposed end of the trans-abdominal gastric surgical system; the revealed matched pairs of suture thread proximal and distal portions are pulled in a direction away from the patient, thereby removing the trans-abdominal gastric surgical system from the patient; and closing the incision by suturing the suture threads in a position that is outside the abdominal wall thereby closing abdominal wall incision and securing the anchor, and thereby the gastric balloon, to the gastric surface.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

BRIEF DESCRIPTION OF THE DRAWINGS

FIG. 7A illustrates use of the transabdominal gastric cannula that can provide pre-sutures through an anchor mount. FIG. 7B illustrates how the presutures may be used to pull the gastric anchor toward the gastric wall to secure the balloon to the gastric wall via the anchor. FIG. 7C shows a three-ring anchor embodiment, and the anchor that is secured within the gastric wall by the sutures.

DETAILED DESCRIPTION OF THE INVENTION

Figure 1:
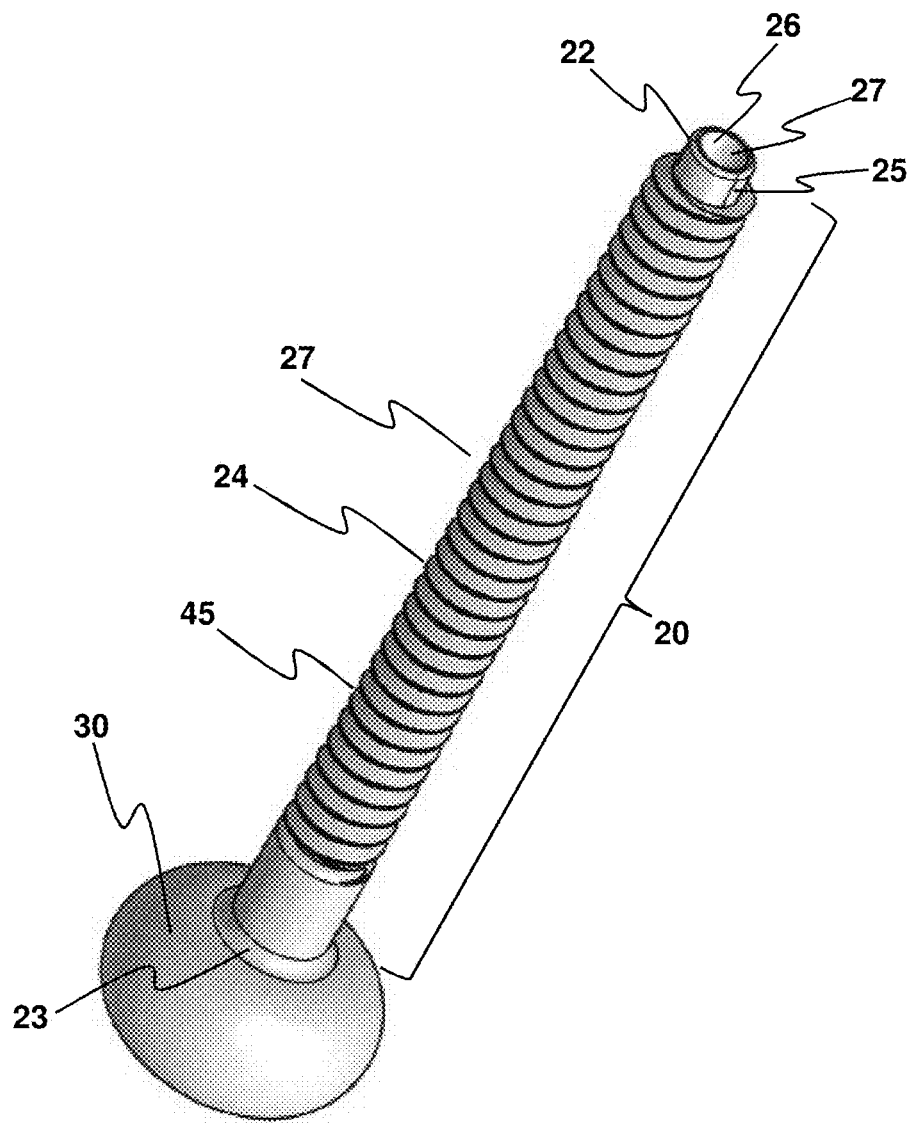
FIG. 1. Perspective view of a trans-abdominal gastric surgical system without an external anchor.

In general, the terms and phrases used herein have their art-recognized meaning, which can be found by reference to standard texts, journal references and contexts known to those skilled in the art. The following definitions are provided to clarify their specific use in the context of the invention.

"Obesity" refers to a patient that is diagnosed as overweight, including morbidly obese or at least non-morbidly obese, including as being overweight with a body mass index in a range of about 30-35, and is desirous of losing weight.

"Treating" refers to the use of the systems described herein that are functionally equivalent to gastric restriction via the use of a deployable gastric space occupying device described herein as a size-varying gastric balloon. The balloon is inserted into the patient in an uninflated state, and subsequently inflated to occupy a substantial fraction of the stomach lumen.

"Low profile" refers to transabdominal gastric cannula having minimal protrusion out of the patient and/or into the stomach lumen. In an embodiment, the protrusion is less than 1 cm, or less than 5 mm from a corresponding surface.

"Proximal stomach portion" refers to that portion of the stomach which is between the esophagus sphincter and the closest point of the gastric balloon, or to the annulus entry.

"Distal stomach portion" refers to that portion of the stomach which is between the pyloric sphincter and the closest point of the gastric balloon, or to the annulus exit.

"Constrained movement" refers to the balloon, and portions thereof, having a degree of movement to accommodate the ebb and flow of peristalsis, but that ensures the prevention of balloon distal migration and attendant side-effects related thereto. In contrast, balloons that are substantially constrained with a rigid and stationary anchor tend to suffer gastric wall irritation and other side effects, thereby decreasing long-term efficacy.

"Long term use" refers to a time period sufficient to achieve a measureable decrease in patient weight, such as for a time period on the order of weeks or months. An important aspect of the balloon systems provided herein is the ability to reliably position the balloon in place to avoid the drawbacks of conventional balloon systems that tend to migrate toward the pyloric sphincter, such as during peristaltic movement of food through the GI-tract. The systems provided herein, including specially constructed gastric balloon anchors in combination with the transabdominal gastric cannula, facilitate reliable balloon anchoring to the gastric wall to avoid such unwanted migration.

"Bumper" refers to a shape of the internal anchor outer surface that is substantially curved and configured to provide reliable contact with an inner surface of a biological tissue, such as the stomach wall or peritoneal surface.

An "internal anchor" of the present invention is the element that is positioned in the body and that anchors the device to an inner surface of the body, in combination with the external anchor. "Adjustable" or "deployable" internal anchor surface shape refers to an internal anchor that can be adjusted or actuated from a first state or shape to a second state or shape. For example, a balloon-type internal anchor can have a surface shape that is adjustable by varying the pressure in the internal volume encompassed by the balloon surface or deployable by inflating from an uninflated state. An umbrella-type mechanism may be adjusted to provide surface shape adjustability in curvature. This aspect also facilitates control of the total surface contact area between the internal anchor surface and the corresponding biological surface, including the stomach or peritoneal wall.

A gastric balloon "anchor" refers to the element that reliably and controllably connects the gastric balloon, specifically a deployed gastric balloon, to the gastric wall. As desired, multiple anchors can be used, with the anchors designed to provide constrained motion of the balloon while avoiding gastric irritation and unwanted balloon motion.

"Flexible" refers to shape deformation under an applied force. Accordingly, a flexible anchor or flexible bumper refers to an anchor or bumper whose shape can at least partially conform to increase the magnitude and reliability of the contact area between the anchor and the corresponding biological surface. A flexible introducer, refers to the ability to deform in order to navigate the contour of a patient's anatomy for system introduction. One quantitative indication of flexibility is Young's modulus (defined as stress/strain). In an aspect, the introducer is formed of a polymer material having a Young's modulus that is less than or equal to 10 GPa, less than or equal to 10 MPa, or less than about 1 MPa, or any other range that provides the desired functional outcome of system flexibility during introduction along the esophagus.

Similarly, the dimensions and geometry of the introducer in combination with the material properties may provide a bending moment useful for system introduction to the gastric environment via the esophagus. "Bending moment" refers to the force on a portion of the introducer that generates a corresponding deflection of the introducer. The bending moment may be quantified based on a cantilever approximation, with an introducer having one end fixed, such as the proximal end that is connected to the cannula, and the other end such as the distal end that is free to move. The bending moment is selected so that a typical force experienced when introducing the system into a patient to follow contours of the esophagus, the system correspondingly bends or deflects to follow the contours and facilitate introduction and minimize unwanted forces on the esophageal wall.

"Removably connected" refers to a configuration of elements, wherein the elements can be temporarily connected to each other and, as desired, removed from each other without adversely impacting the functionality of other elements of the device. "Translationally connected" refers to a configuration of elements, wherein motion of one element is substantially unidirectional and parallel with respect to another element, wherein movement of one element does not affect each element's functionality. "Operably connected" refers to a configuration of elements, wherein an action or reaction of one element affects another element, but in a manner that preserves each element's functionality. For example, a pressure port operably connected to a cap refers to the ability to monitor or effect pressure change without impacting the functionality of the cap, including having other ports for introduction of medical instruments.

"Fluidically connected" refers to a configuration of elements, wherein a fluid (e.g., liquid, gas or viscoelastic material) in one element is able to enter another element in a manner that does not affect each element's functionality. For example, a fluid conduit that is fluidically connected to a balloon does not affect the balloon's ability to be positioned and inflated/deflated.

"Unitary material" refers to two elements that are integrally connected, such as an internal anchor and cannula that are formed from one piece. This is in contrast to identical material that may be more permanently connected, such as by an adhesive or bond, or removably connected such as by a threaded connection.

"Capture element" refers to the portion of the introducer on which a force is exerted so as to advance the system into the patient, such as down the esophagus, into the gastric environment and through the abdominal wall so that one end of the system remains in the patient and the opposite end is accessible from the environment that is outside a patient's body. The invention is compatible with a range of capture elements, so long as the ability to reliably introduce the system by retrograde introduction via the esophagus is not impacted. Specific examples include, but are not limited to, a wire loop, a suture, a connection mechanism such as snap-fit, magnets, threaded attachment, clamp or fasteners.

"Fluid" refers to a material that may be removed or introduced from a volume to effect a change in pressure, including a material that flows under an applied force. Depending on the application of interest, the fluid may be a gas, a liquid, a gel, or a combination thereof.

Unless defined otherwise, "substantially" refers to a value that is within at least 20%, within at least 10%, or within at least 5% of a desired or true value. Substantially, accordingly, includes a value that matches a desired value.

Example 1: Trans-Abdominal Gastric Surgical System

Figure 2:
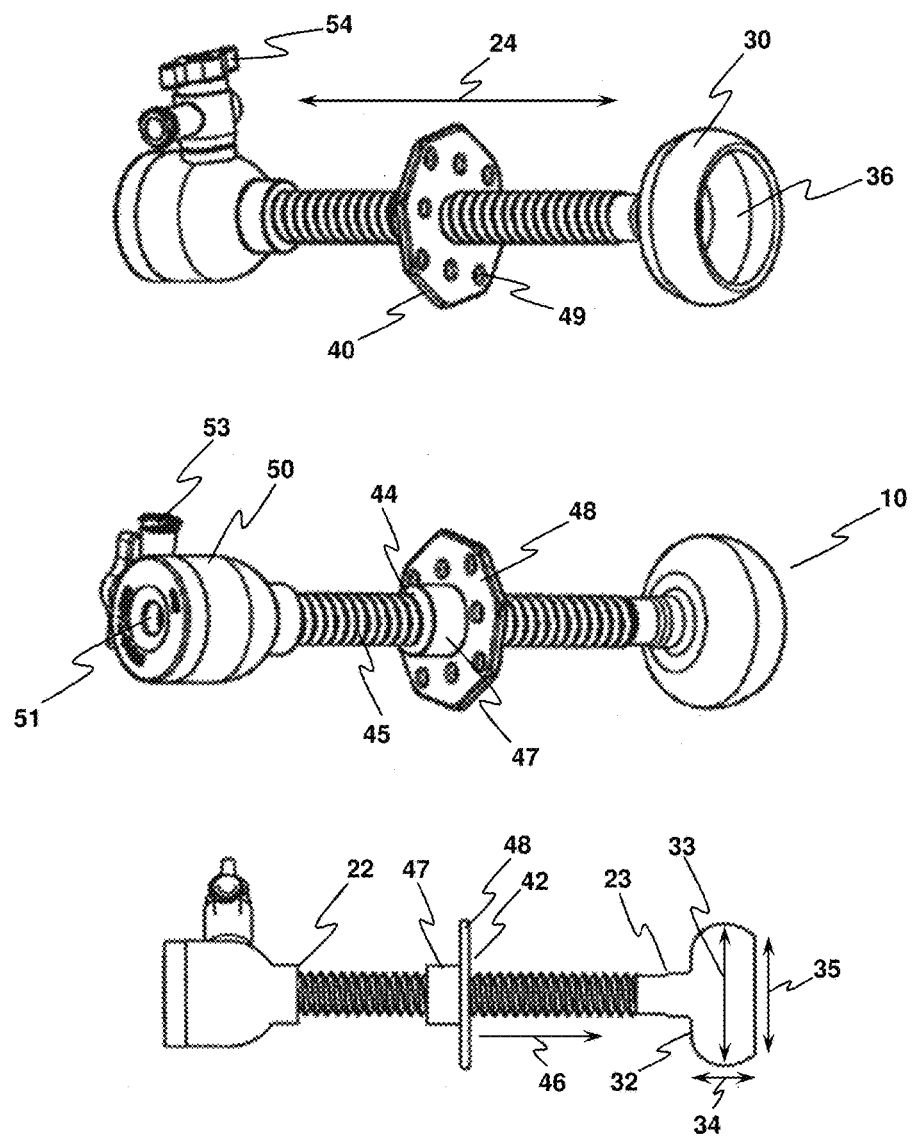
FIG. 2. Views of a trans-abdominal gastric surgical system with external anchor and cap showing the interior volume of the internal anchor (top panel), the instrument port (middle panel) and a side view (bottom panel).
Figure 3:
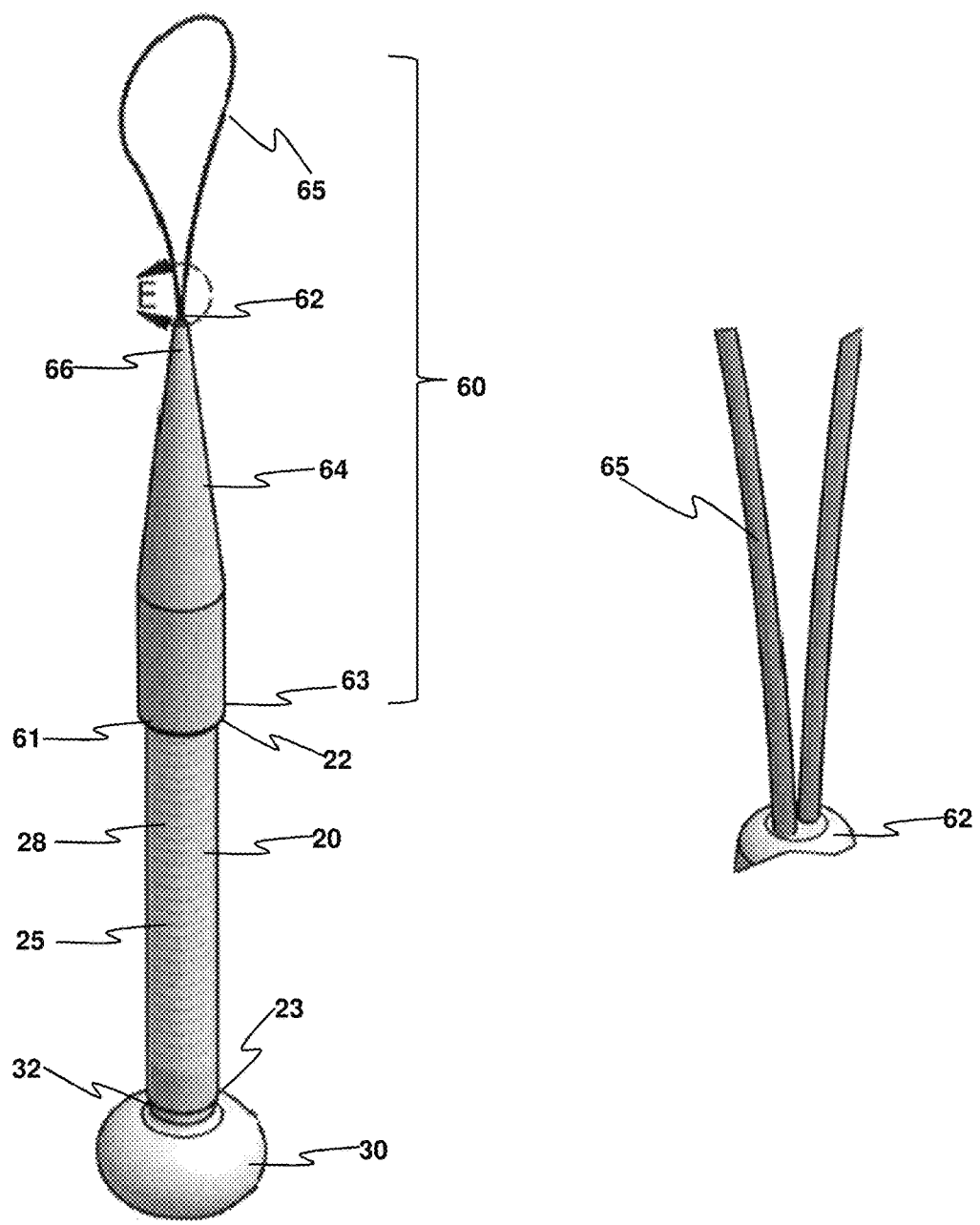
FIG. 3. A trans-abdominal gastric surgical system and connector element ready to receive a guidewire for insertion into a patient (left panel). The right panel is a close-up view of the capture element connected to the introducer distal end.

Referring to FIGS. 1-3, a trans-abdominal gastric surgical system 10 or generally, system, has a cannula 20 with an outer end 22, an inner end 23 and a central portion 24. Central portion has an outer-facing surface 25 that extends between the inner end and the outer end and an inner-facing surface 26 that defines a lumen 27 configured to receive a portion of a medical instrument 12 (see, e.g., FIG. 8) that traverses between the cannula outer and inner ends, such as from outside the patient to inside the patient. Lumen 27 is also referred herein as a working channel during use, such as a working channel to the stomach lumen. An internal anchor 30 is connected to the inner end 23 and has a surface shape 32 configured to secure the system against an interior surface of a gastric wall or peritoneal surface. An external anchor 40 is removably and translationally connected to the cannula outer-facing surface and has a surface shape 42 configured to secure the system against a skin surface (FIG. 2). Accordingly, FIG. 1 illustrates an external anchor removed configuration, because external anchor 40 is not connected. This is in contrast to FIG. 2, where external anchor 40 is connected and is capable of being positioned at various longitudinal distances along cannula axis, as indicated by arrow 46 directed along the system longitudinal axis.

As illustrated in FIG. 2, the internal anchor may correspond to a bumper having a curved outer surface 32 with a maximum diameter 33, a height 34, an open exit diameter 35, and a hollow interior volume 36.

Referring to FIG. 2 (external anchor connected configuration), external anchor 40 may be a disc having an inner-facing surface 43 that defines a passage 44 for receiving a cannula, more specifically cannula central portion 24. The translational connection between external anchor 40 and cannula 20 may be a matched internal thread 28 and external thread 45, illustrated as being on the inner-facing surface 43 of external anchor 40 and outer-facing cannula surface 25 of cannula 20, respectively. In this manner, the external anchor may be positioned to have any desired separation distance from the internal anchor by moving along the cannula in a longitudinal direction, as indicated by arrow 46. Other translational connections may be employed, including a tight friction fit, clamp, snap-fit, fasteners, set screws, or the like. The external anchor 40 may have a central body 47 in which the passage 44 is disposed and a flange 48 connected thereto. A plurality of second passages 49 may extend through the flange, for facilitating suture placement and system removal.

To provide controlled access to the cannula from the outer end 23 a cap 50 may be removably connected to the cannula outer end. The cap may have one or more instrument ports 51 through which one or more medical instruments 12 may be inserted. The instrument port 51 may be formed from a memory sealant material. A pressure port 53 may be connected to the cap 50 to control pressure, such as by removal or introduction of a fluid to cannula inner end 22, and thereby to the gastric environment or a fluid conduit connected thereto which, in turn, is fluidically connected to a balloon. Controlled access to the cannula may also be provided by a stop-cock 54 type mechanism connected to the cap.

Figure 19:
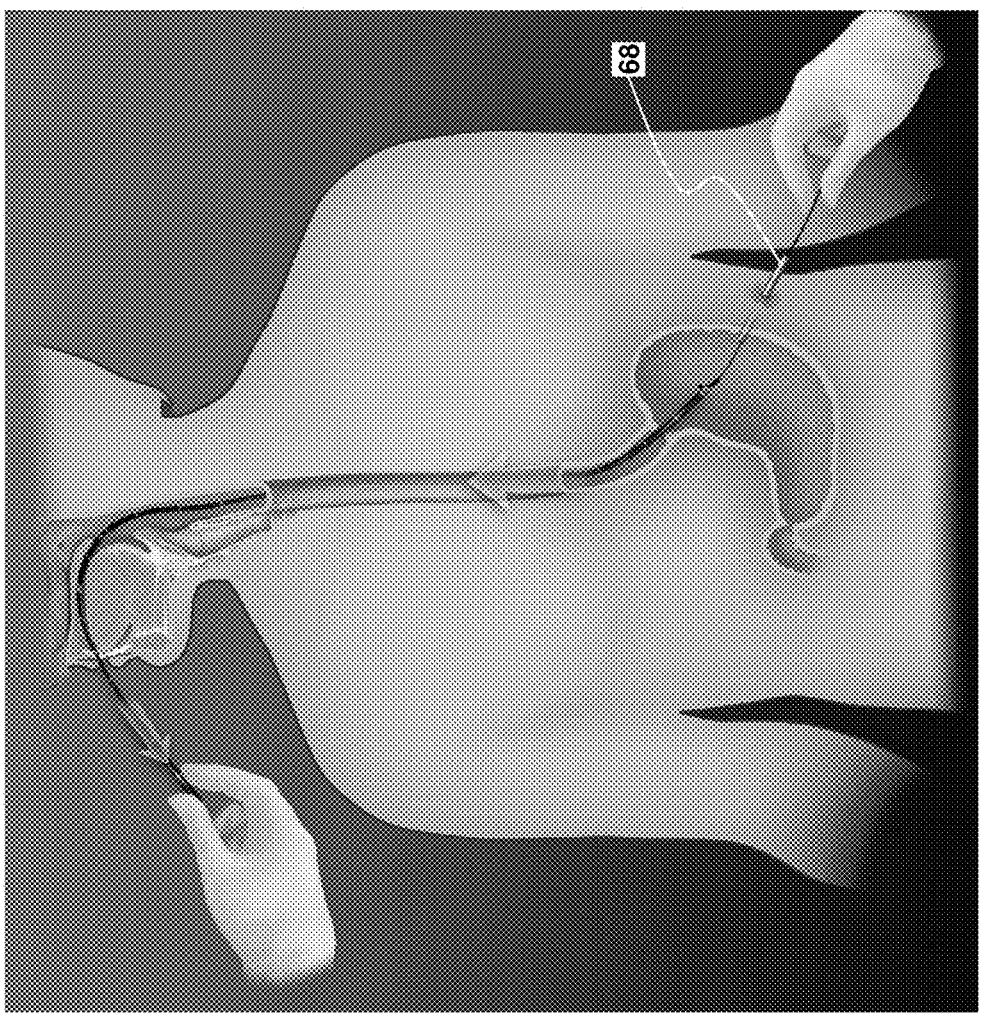
FIG. 19. Guidewire insertion through the abdominal and gastric wall, up the esophagus and out of the patient mouth.

To facilitate system introduction to a patient, an introducer 60 may be used. Referring to FIG. 3, introducer 60 is removably connected to the system, such as when the external anchor 40 is removed as shown in FIG. 1, so as to provide a system that may be introduced to the gastric environment by retrograde introduction past a patient's oropharynx and into the gastric environment. Accordingly, FIG. 1 may be further described as in an introducer-removed configuration and FIG. 3 in an introduction ready configuration that is ready to be inserted into the patient by retrograde introduction. The introducer may have a receiving opening 61 that removably receives the cannula outer end 22 and a portion of the cannula central portion 24. The receiving passage may have a threaded portion, such as to removably engage with the cannula central portion, in a manner similar to that of the external anchor and cannula central portion. A distal end 62 may connect to a capture element 65, illustrated as a wire loop. A proximal end 63 may contain the receiving opening 61, and a tapered central portion 64 that extends between the distal 62 and proximal 63 ends. In this manner, a guidewire 68 (see, e.g., FIG. 19) may be used to pull the introducer and system combination into the gastric environment. The tapered end of the introducer may then be pulled through the incision in which the guidewire passes to provide a reliable contact area between the internal anchor and the gastric wall, as well as gently expanding the abdominal opening to ensure a good fit in the abdominal wall. Similarly, reliable contact area between the internal anchor and an inner facing surface of the peritoneal cavity may be established for an equivalent incision for a guidewire provided therein.

Once the system is positioned accordingly, the introducer may be removed to provide an introducer-removed configuration 67 that is ready to receive the external anchor 40 (see, e.g., FIG. 23).

Example 2: Size Varying Gastric Balloon

Figure 4:
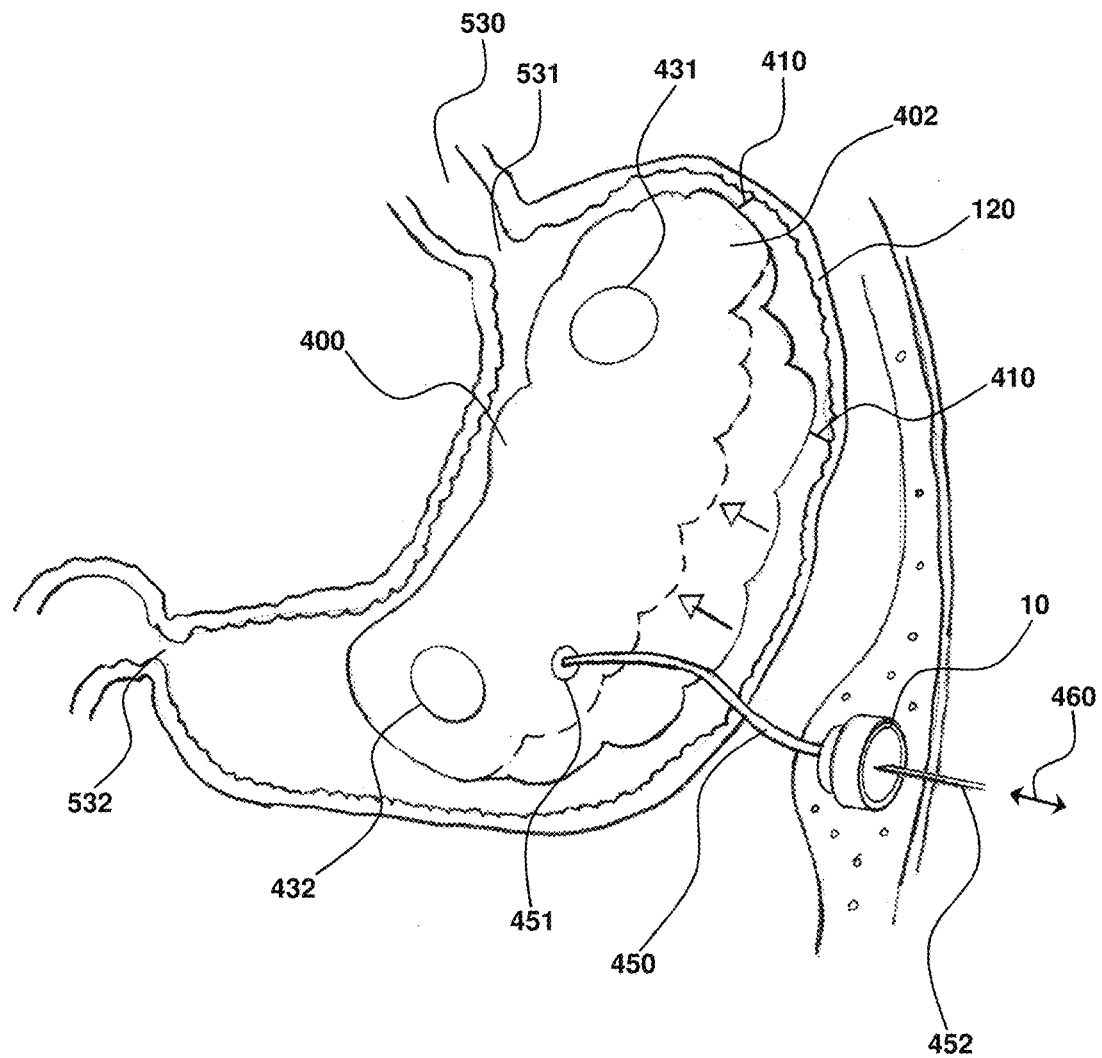
FIG. 4. Deployed annular balloon connected to a single fluid conduit and tethered to a subcutaneously placed port for inflation or deflation of the balloon.
Figure 5:
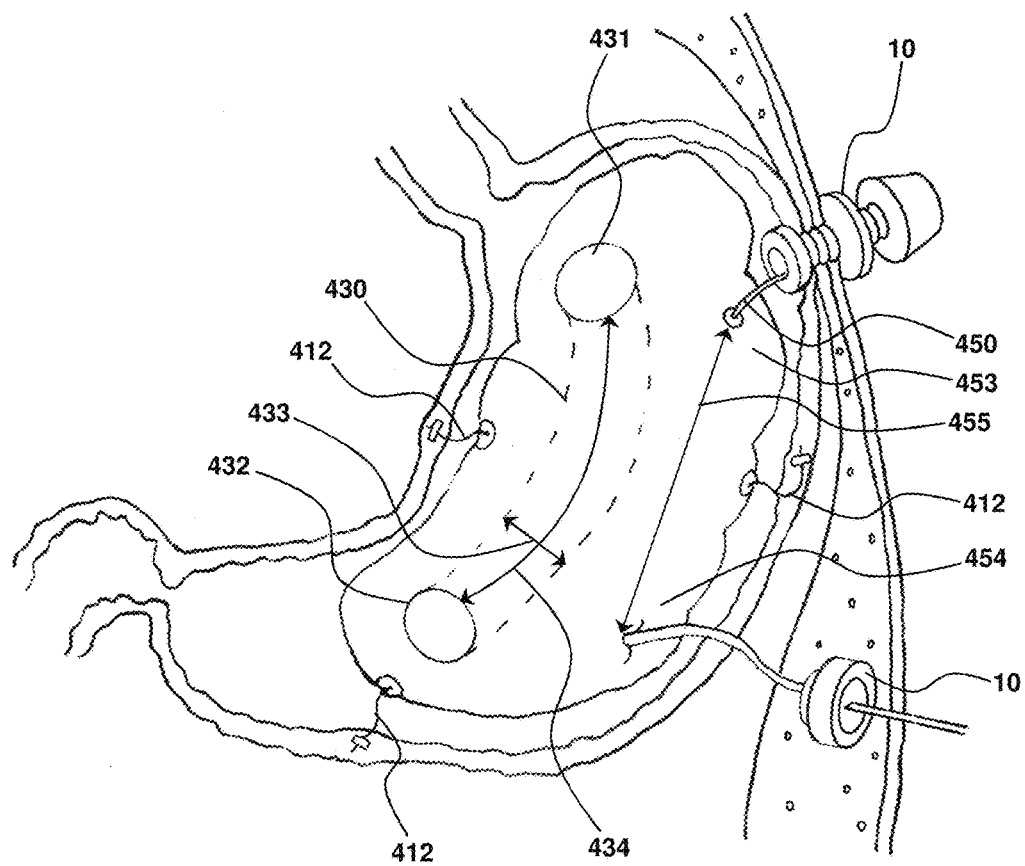
FIG. 5. Deployed annular balloon connected to one fluid conduit and one transabdominal gastric cannula.

One example of a gastric balloon system for obesity treatment is illustrated in FIGS. 4-5. A size-varying gastric balloon 400 is provided with a trans-abdominal gastric cannula or subcutaneous port 10, including the trans-abdominal gastric system discussed in Example 1 and FIGS. 1-3. The balloon 400 has an internal volume 402 defined by balloon surface 410. One or more gastric balloon anchors 412 connected to the balloon can connect to the gastric wall and/or the cannula 10 to reliably position and anchor the balloon in the gastric environment.

For balloon inflation/deflation, a fluid conduit 450 may traverse the gastric cannula 10 and fluidically connect to the balloon at a first fluid end 451 and have a second end 452 positioned externally to the patient. This facilitates introduction or removal of fluid, thereby controlling the shape of the balloon implanted in the stomach 120. A fluid source for introducing and/or removing a fluid, such as a liquid or a gas, is indicated by arrow 460.

FIG. 5 illustrates that the balloon anchor may correspond to a fluid conduit 450 connected to the transabdominal gastric cannula 10, such as in an anterior portion 453 of the balloon and stomach wall. In this manner, the fluid conduit may functionally provide a tether type mechanism, thereby providing additional positional control of the balloon. In addition, a fluid conduit may connect to a cephalad portion 454 of the balloon. FIG. 5 illustrates a two gastric cannula 10 and two fluid conduit 450 embodiment, with the first fluid ends separated by a fluid conduit separation distance 455. In this manner, a plurality of inflation/deflation ports is provided. For example, during use one of the ports may be accessed endoscopically, as desired, particularly for embodiments where the gastric cannula and an associated percutaneous fluid cannula have been removed.

Figure 6:
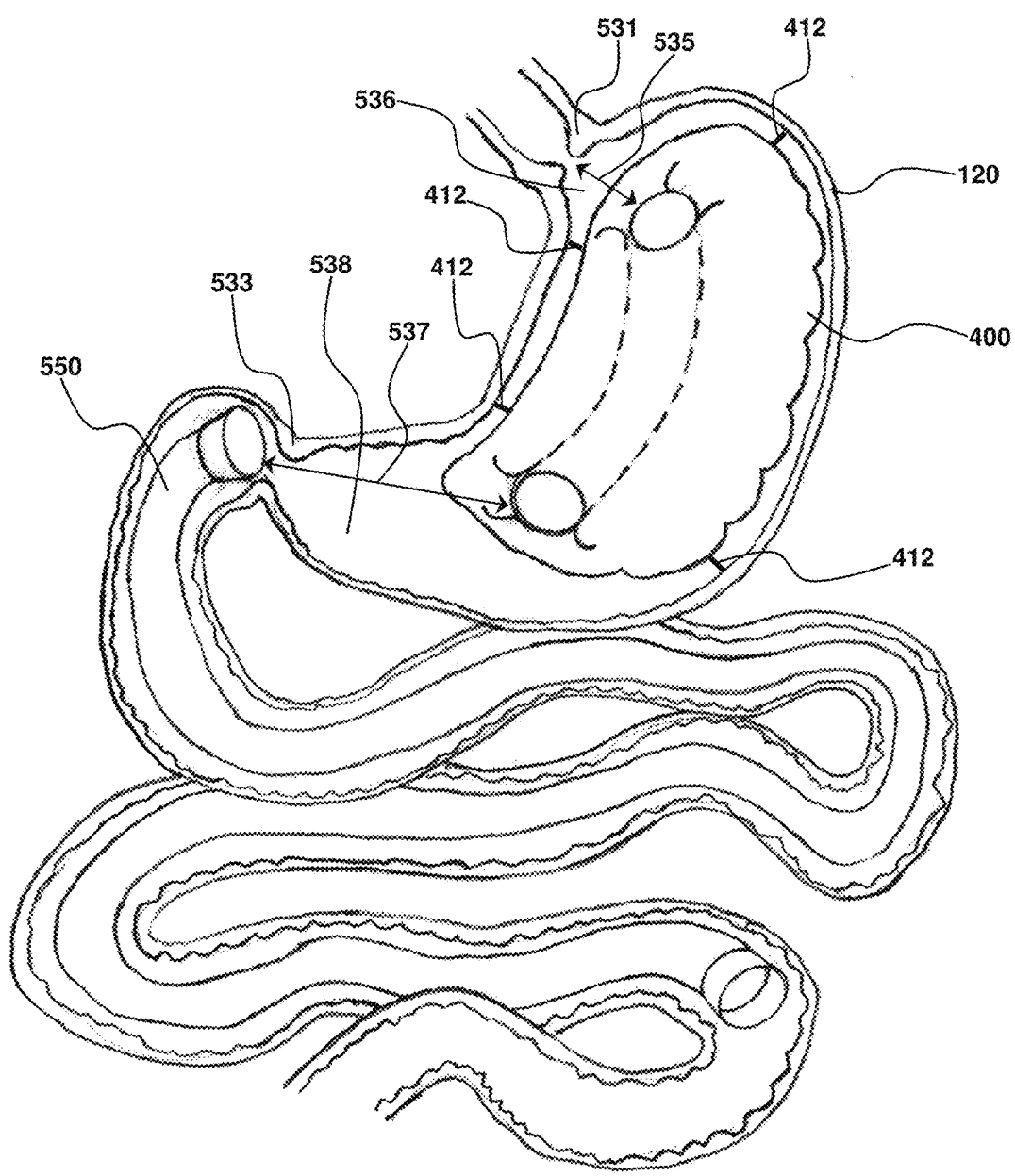
FIG. 6. Deployed annular balloon anchored to the stomach wall, with malabsorption sleeve, and the transabdominal gastric cannula removed from the patient.

FIG. 6 illustrates the embodiment where after balloon insertion and inflation, the transabdominal gastric cannula 10 (see, e.g., FIGS. 4-5) may be removed, leaving the deployed and inflated gastric balloon 400 anchored to the stomach wall 120 by a plurality of anchors 412. Alternatively, the gastric cannula 10 may remain in the patient. In those situations, the gastric cannula is provided in a low-profile to increase patient comfort.

Figure 10:
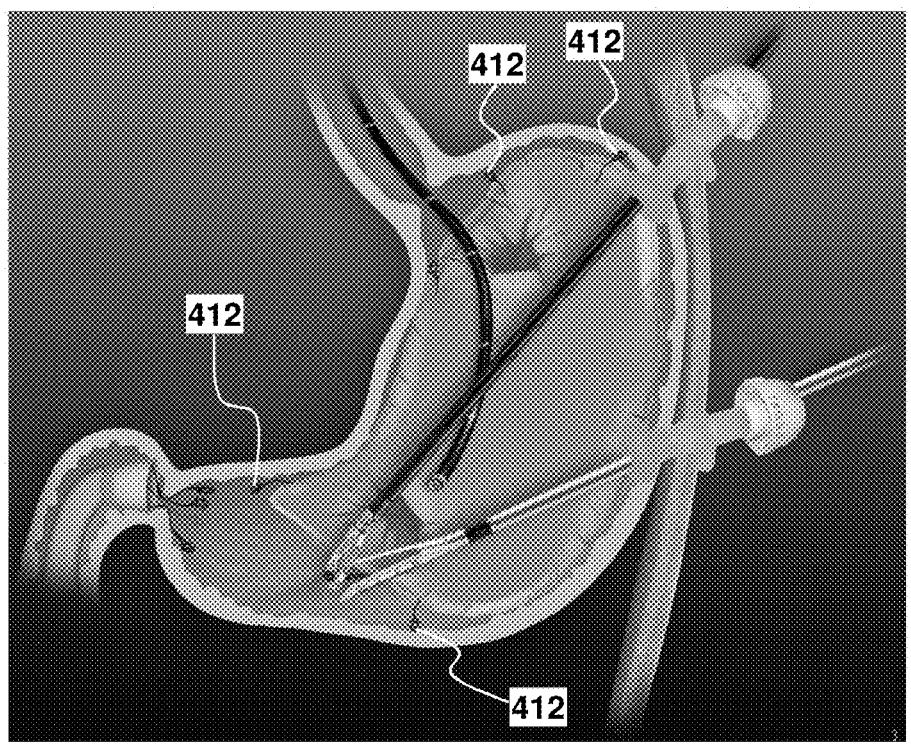
FIG. 10. The system of FIG. 9, illustrating instrument triangulation on an anchor to anchor the balloon to the gastric wall.
Figure 11:
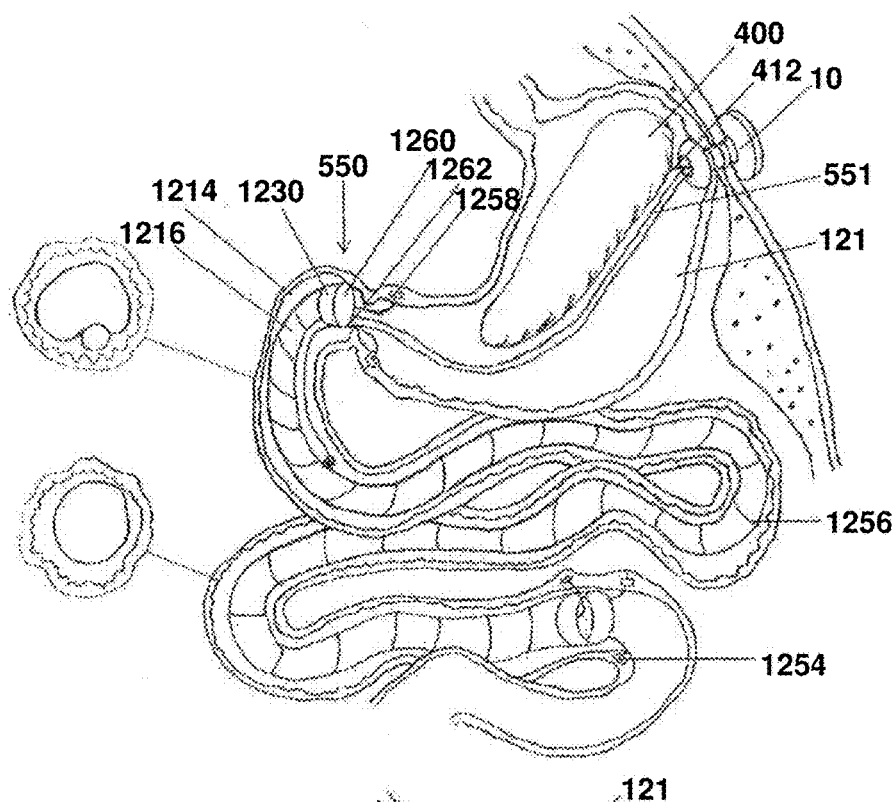
FIG. 11. Partial balloon deployment in the stomach and elongated malabsorption sleeve deployed in the duodenum connected via a tether to the transabdominal gastric cannula.
Figure 12:
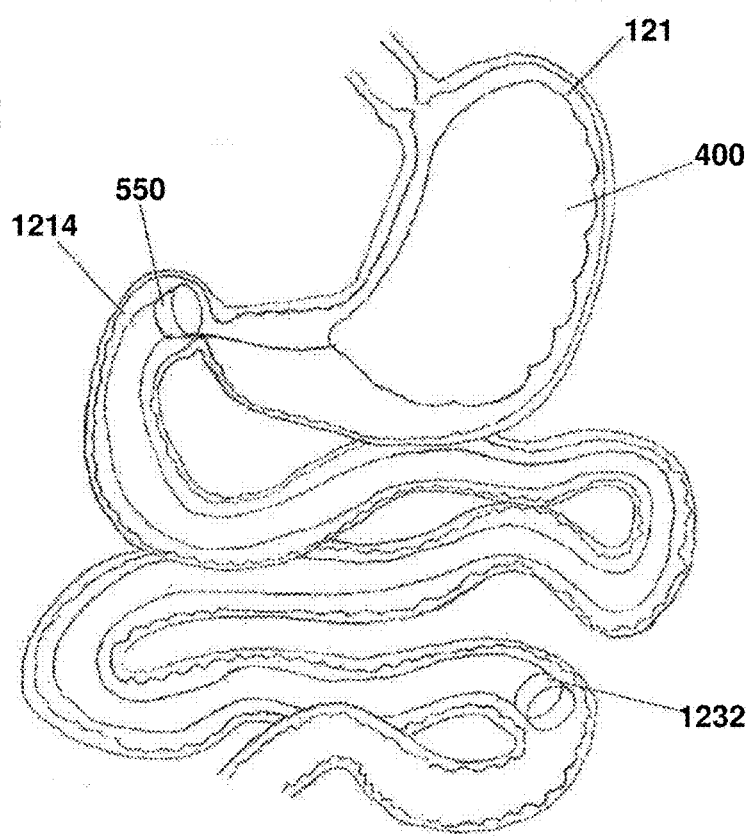
FIG. 12. Deployed non-annular gastric balloon with an elongated gastric sleeve connected thereto.

As illustrated in FIGS. 11-12, the balloon 400 may have a non-annulus shape. Alternatively, the balloon may have an annulus 430, as illustrated in FIGS. 4 and 10. Annulus has an entry 431 and exit 432 aligned with the esophageal 530 exit or sphincter 531 and the stomach exit or pyloric sphincter 533, respectively. The annulus is configured to facilitate passage of fluids and food solids from the esophagus and out of the stomach and is optionally defined in terms of an average diameter and length, as indicated by arrows 433 and 434, respectively (FIG. 5).

An important aspect of the systems and methods is the ability to position the balloon such that when it is deployed and during use, including long-term use on the order of weeks or months, including greater than 6 months to two years or more, the balloon's position is maintained within the stomach. Referring to FIG. 6, a desired position can be defined in terms of a separation distance from the esophageal sphincter 531 and from the pyloric sphincter 533, as indicated by arrows 535 and 537, respectively. An alternative description of the balloon position is provided in terms of volumes and fractional portions thereof. For example, when fully deployed, the balloon may occupy at least 75% of the stomach lumen. The unoccupied fraction of the stomach, however, is not uniform. The major unoccupied portions are in a proximal stomach portion 536 adjacent to the esophageal sphincter 531 and the distal stomach portion 538 adjacent to the pyloric sphincter 533. Of those two portions, however, the distal stomach portion 538 has a substantially larger volume than the proximal stomach portion 536. This is a reflection that the instant invention ensures there is sufficient separation distance from the pyloric sphincter to minimize risk of a gastric blockage.

Any of the systems provided herein may be used with an elongated sleeve, such as depicted by 550 in FIG. 6, and as further explained in U.S. Pub. No. 2014/0276338, explicitly incorporated by reference for the sleeves and related methods and disclosed therein.

Figure 8:
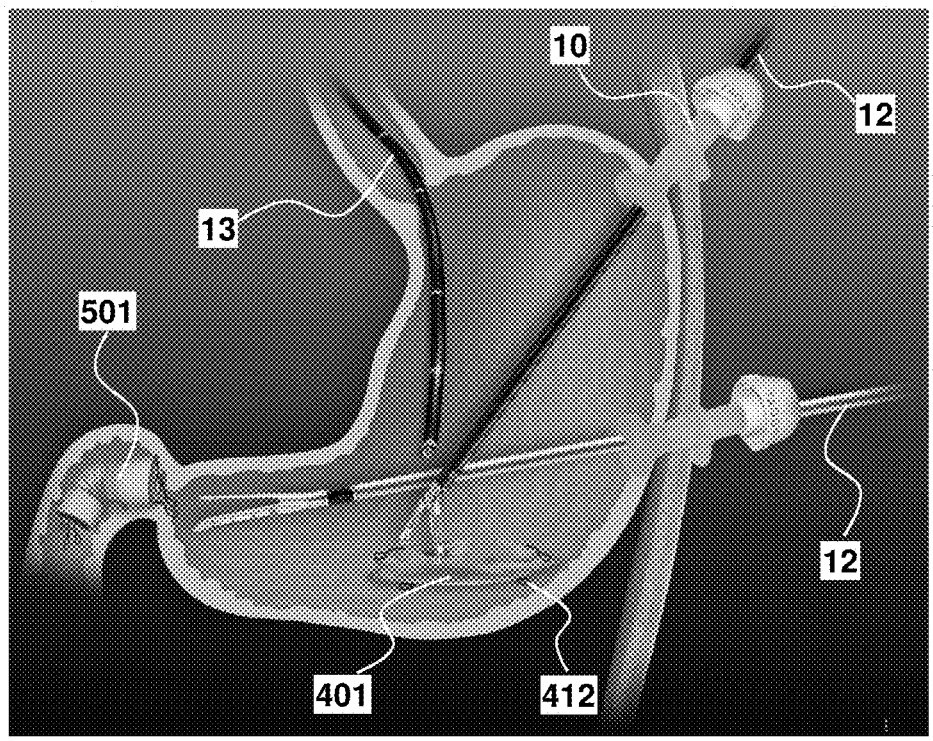
FIG. 8. Two transabdominal gastric cannula with medical instruments disposed therethrough, and undeployed gastric balloon in the gastric lumen and unextended elongated sleeve in the lumen of the upper GI tract. Also shown is an endoscopic instrument, such as a fiber optic light source.
Figure 9:
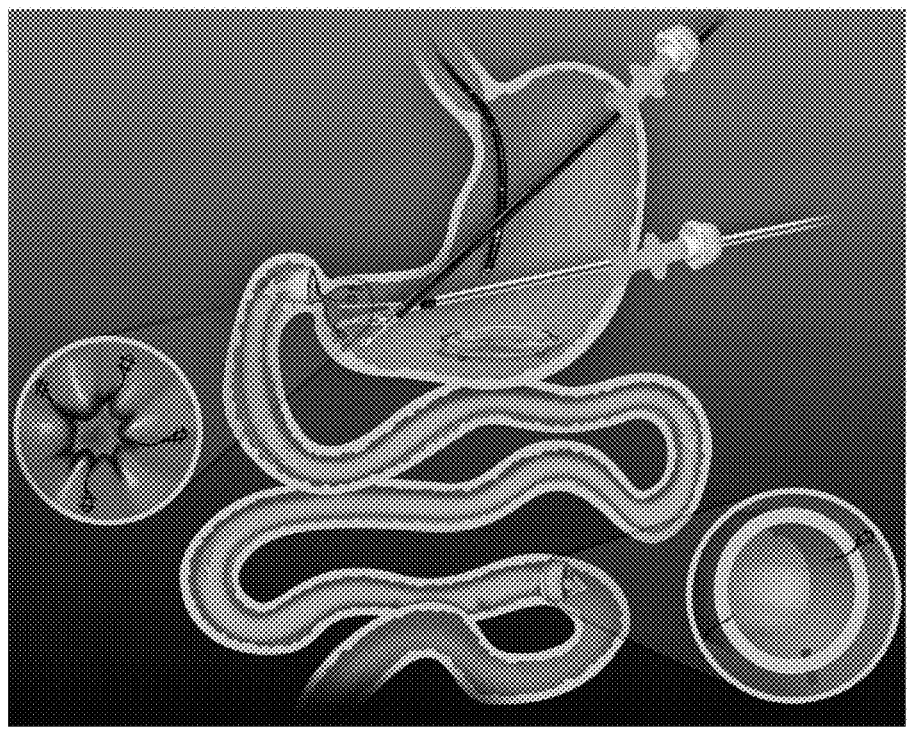
FIG. 9 illustrates use of medical instruments for connecting anchors to the gastric wall. Inset is a view down the lumen of the pyloric sphincter illustrating four anchors.

Referring to FIGS. 8-10, manipulation of the balloon and sleeve is illustrated via medical instruments 12 inserted through one or more transabdominal gastric cannulas. In FIG. 8, illustrated is an undeployed balloon 401 and sleeve 501. A medical instrument 12 through one of the transabdominal gastric cannula is used to secure sleeve anchors for sleeve deployment, as illustrated in FIG. 9. As shown in FIG. 10, the medical instruments 12 traversing the cannula of 10 are used to secure balloon anchors 412 to the gastric wall in strategic locations to ensure appropriate separation distances from the stomach entry and exit and corresponding appropriate volumes for proximal 536 and distal 538 stomach portions. This anchoring may occur prior to balloon inflation, after balloon inflation, during an intermediate semi-inflated balloon configuration where the balloon is only partially inflated, or any combination thereof.

FIG. 11 illustrates a gastric balloon 400 in the stomach lumen 121 tethered to a transabdominal gastric cannula 10 via anchor or tether 412. As explained further in U.S. Pub. No. 2014/0276338, tube or catheter 551 may be operably connected to elongated sleeve 550 positioned in the upper GI region of the small intestine having a proximal end adjacent to the pyloric sphincter secured to the gastric wall. Also illustrated, for clarity, is small intestine 1214, malabsorption sleeve 1216, collar member 1230, central aperture 1260, catheter passage 1262, anchor mechanisms 1258, distal anchor weight 1254, and lumen support element 1256. FIG. 12 illustrates the sleeve 550 having a distal end 1232, with the sleeve connected to a deployed balloon 400 and with the transabdominal gastric cannula 10 of FIG. 11 removed. As discussed, the balloon 400 may be anchored to the gastric wall by one or more gastric balloon anchors.

The intra-gastric balloons (IGB) described herein are preferably smooth, seamless, and constructed of a material that is long-lasting, inert, non-toxic, having low ulcerogenic potential while being resistant to gastric acid. The balloon may have a radiopaque marker to assist with post-procedure imaging. The configuration of the systems provided herein ensures there is a low obstructive potential. The balloon is adjustable to a variety of sizes and can be filled with a fluid that is a liquid or air. A self-sealing valve may be incorporated to facilitate volume control and adjustment. The balloon is non-permanent and can be readily removed as desired, such as by endoscopic procedures with an endoscopic catheter.

Example 3: Gastric Balloon Anchors

Also provided herein are gastric balloon anchors, including anchors that may be used with conventional balloons, or any of the balloons herein. For retrofitting, an anchor may be affixed to an outer surface of a balloon. Alternatively, balloons may be made with the anchor an integral part thereof, such as an anchor having one end embedded within or through the balloon wall.

The anchors may be manufactured such that they are an integral part of the balloon, including by having one end at least partially or fully embedded in the balloon wall. Alternatively, the anchors may be supplied as an after-market addition, thereby transforming conventional balloons into a balloon compatible with the systems and methods provided herein. The anchors are configured to have a certain amount of give at either end, to ensure there is not an over-tightness or rigidity at the site of attachment. For example, the anchor retains an ability to move in relatively small distances, including horizontally, vertically and/or rotationally. A small distance refers to the movement of the balloon that accommodates the ebb and flow of gastric motion, e.g., peristalsis, but not so much as to result in an unwanted distal migration of the balloon toward the pyloric sphincter. In this manner, the anchor may be incorporated in its attachment to the gastric wall by using the same closure technique as for wall defect closure during cannula removal. For example, the same sutures may serve two functions of: (1) defect closure; and (2) balloon anchoring to the gastric wall. The anchor, and attendant exposed sutures, are biocompatible and able to withstand the acid environment associated with the stomach lumen. There are many possible anchor designs that achieve this function.

Figure 7A:
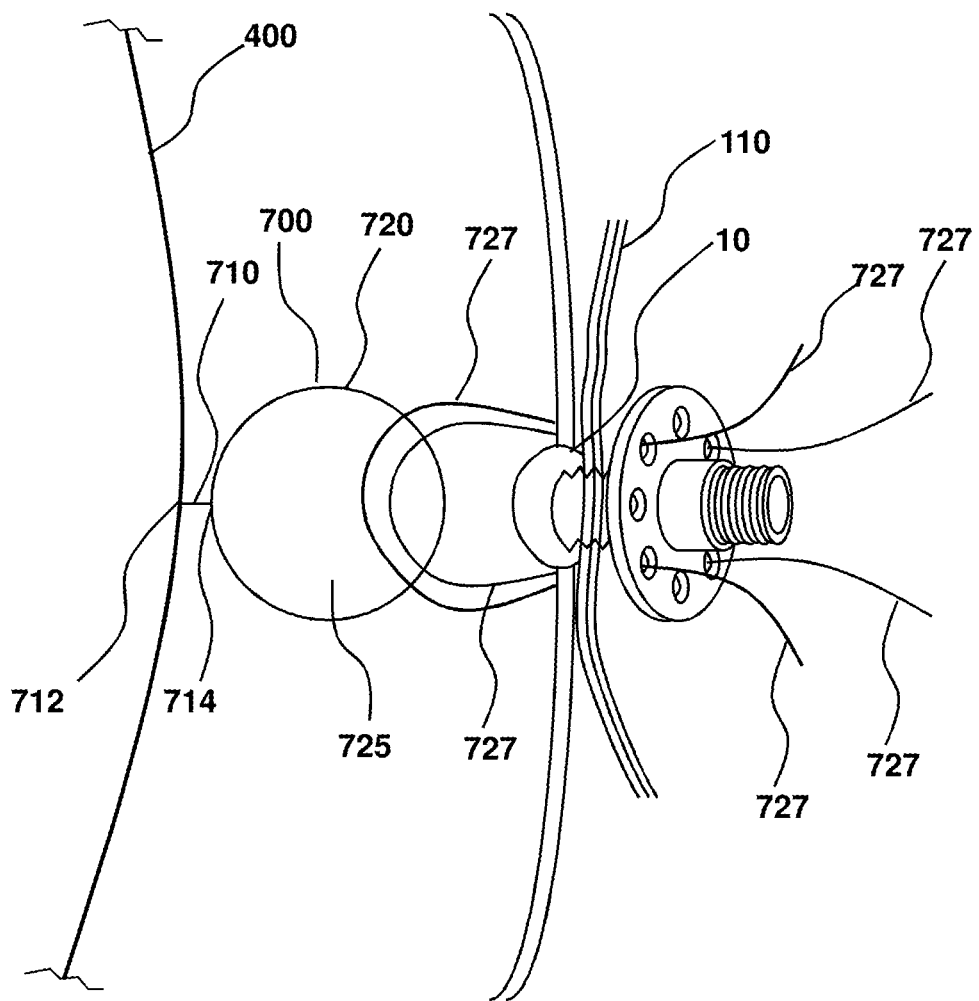
FIG. 7A-7C. Schematic illustration of a gastric balloon anchor and presutures for reliably anchoring a gastric balloon to a gastric wall.
Figure 7B:
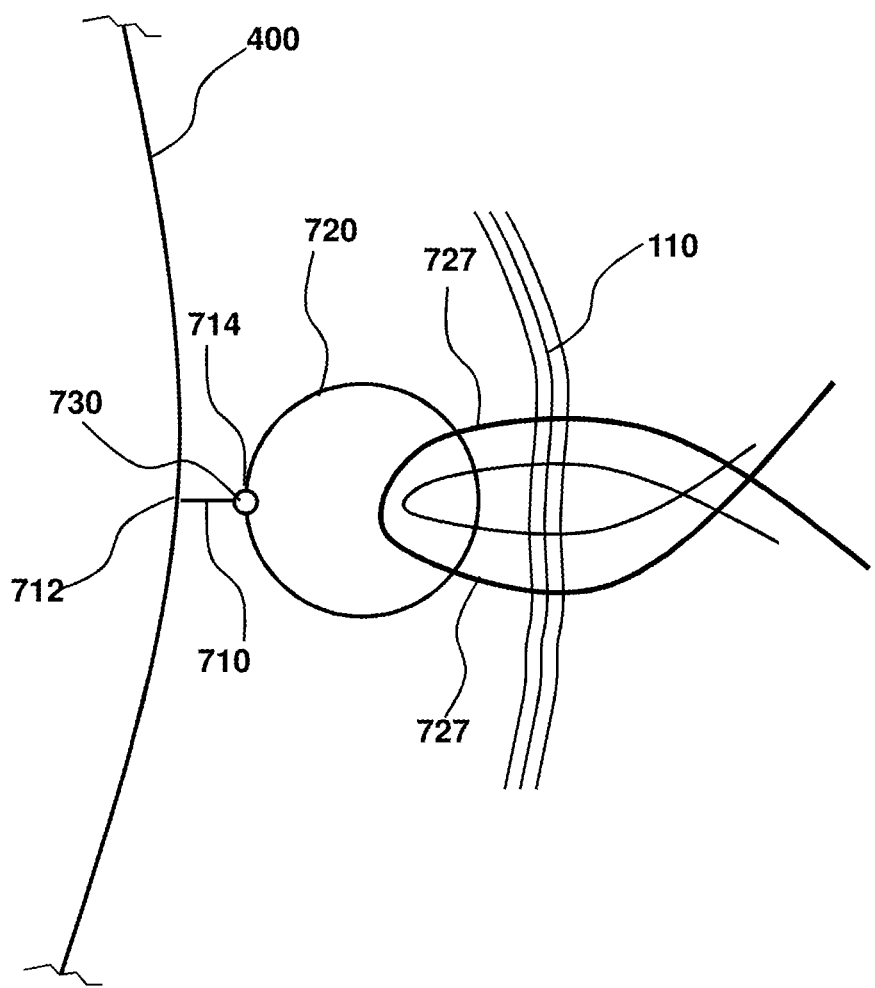
Figure 7C:
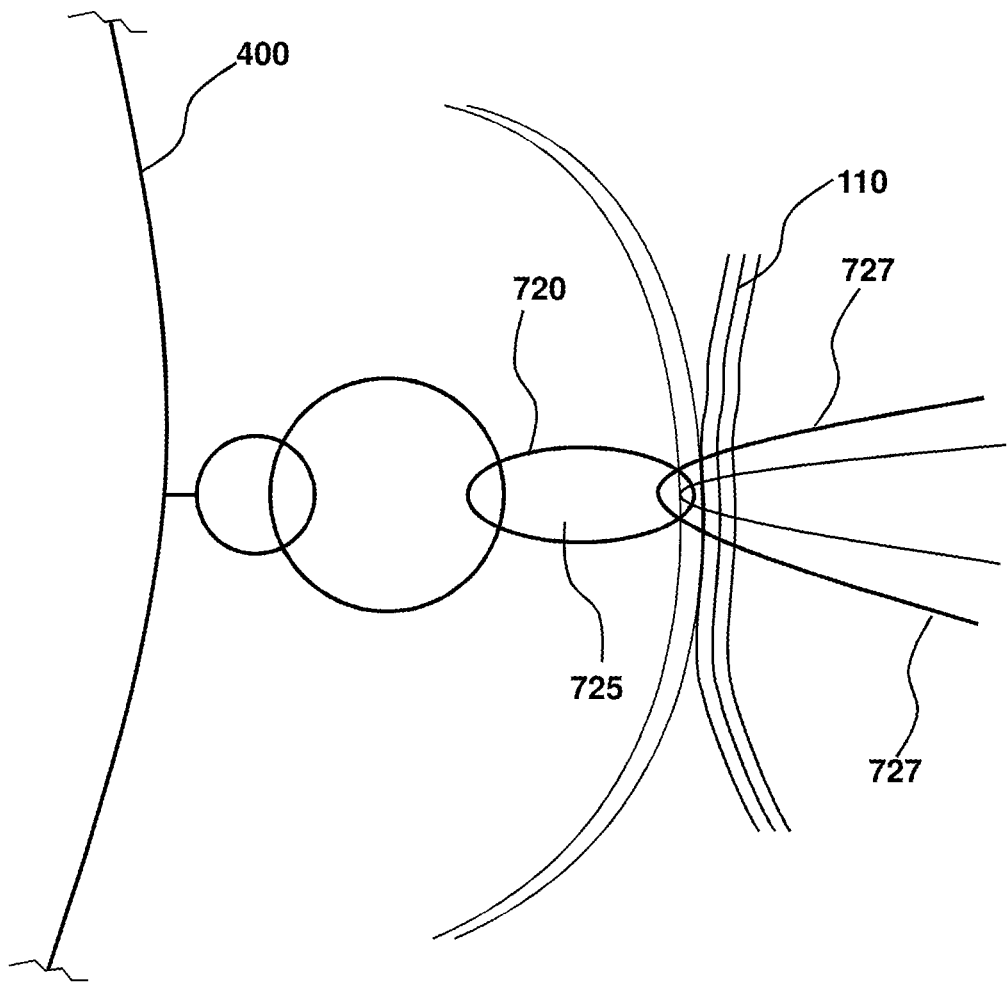

A non-limiting example of such an anchor is provided in FIG. 7A-7C. The anchor 700 facilitates constrained movement of the balloon 400 during use. A fastener 710 may have a first end 712 and a second end 714, wherein the first end 712 is connected to the balloon and the second end to the anchor mount 720, either directly (FIG. 7A) or indirectly via one or more additional anchor elements (FIG. 7B-7C). Anchor mount 720 may have an opening 725 for receiving pre-sutures, illustrated in this embodiment by two pre-sutures 727, that may have matching colors to avoid any confusion as to which ends should be tied together to form complete sutures. Anchor mount 720 is illustrated in FIGS. 7A-7B as ring-shaped. Anchor mount 720 however, can have any of a variety of shapes, particularly for the embodiments where the anchor mount is deformable, such as being formed from suture-threads material that does not substantially degrade in the gastric environment or the gastric wall. For example, FIG. 7C illustrates the anchor mount 720 that is deformed into a non-circular, elongated shape.

The anchor mount may be connected to the fastener second end, such as via a fastener coupling 730. The fastener coupling may itself be a ring or other fastener that allows motion of the anchor ring, such as a rotation type motion about one or more axis. As desired, the presutures and gastric cannula 10 may facilitate anchor mount that is at least partially embedded in the gastric wall (FIG. 7C) and that may extend out from the gastric wall. This anchoring is straightforward, reliable, and automatically achieved as part of the removal of gastric cannula and attendant suturing of the wall defects by presutures 727 (see also FIGS. 13-17). The anchor elements, including anchor mount 720 may be formed from a suture thread or material that does not substantially degrade in the gastric environment. In contrast, the presutures 727 may be bioresorbable. Accordingly, if balloon removal is desired, the anchor elements may be simply cut toward the gastric wall, such as via an endoscopic procedure, and the balloon removed from the gastric wall without any need for a surgical intervention. Any remaining ends of non-degradable suture extending from the gastric wall are relatively small and do not adversely impact the gastric wall or environment. Forming the anchor mount from such a non-rigid and shape-changeable material ensures there is an appropriate amount of give in the anchor ends. In an aspect, the anchor may be formed from one or more rings, such as one ring, two rings or three rings.

As provided herein, the anchor can be formed from a single loop or from multiple loops, including two or three loops, so as to provide the appropriate amount of constrained movement and flexibility between the balloon and gastric wall. In the single loop/anchor embodiment, there may be one central or main anchor. In a triple anchor embodiment, there may be one central or main anchor, with two smaller side anchors. The anchor material may be biocompatible, non-dissolvable suture-type material, which allows the anchor to maintain the balloon in the appropriate location without unwanted balloon migration and still allow some slight "give and take" to prevent gastric wall irritation, torsion, etc. Color coded, such as red and blue sutures, either can pass through a main central ring or a side ring, and then the balloon and anchor will close with the same closure method as described for the transabdominal gastric cannula, with optionally reliable embedding of a portion of the anchor mount in the gastric wall and attendant reliable anchoring of the balloon in the gastric or stomach lumen.

Although the anchor has been described in terms of suture materials, the anchors are compatible with any number of additional elements. For example, a magnetic component may be integrated to the anchor rings and suture, to provide an additional means for securing the anchor to the gastric wall.

The anchor is formed of any material, shape, durometer, size and flexibility, as desired, depending on the application of interest and gastric environment.

The rings are easily clipped when it is time to remove the balloon, thus freeing the balloon from the gastric wall without any need for surgical intervention, as the anchors may be accessed endoscopically. While the anchor connection is illustrated as via a suture through a ring or rings, the invention is compatible with many other connection mechanisms and anchors, including but not limited to a fastener, snap device or a clip device.

Example 4: Closure System Removal and Anchoring

An important benefit of the instant systems and methods is the ability to simply, reliably and robustly close the abdominal incision through which the system traverses, in parallel with balloon anchoring. This is achieved, in part, by the plurality of passages 49 through the flange 48 of the external anchor 40 (FIG. 2). Referring to the flow chart of FIG. 13 and corresponding diagrams of FIGS. 14-17, passages 49 facilitate guided insertion and removal of one or more suture threads 70 76 (FIGS. 14 and 16). In particular, first thread 70 is inserted into first passage 71, such as by a cannulated-introducer needle 80 containing a suture thread proximal portion 74. A suture grasper 81 grabs a suture thread distal portion 75 and pulls the suture thread through second passage 72, that is geometrically opposed to first passage 71. "Geometrically opposed" in this aspect refers to a pair of passages wherein at least a portion of the external anchor central body 47 is disposed therebetween. Accordingly, with the illustrated configuration, the opposed passages may be 180° opposed (see inset of FIG. 14). The invention, however, is compatible with variations on the opposed configuration, so long as a portion of the suture thread traverses the outer-most facing surface of the internal anchor and passes through an anchor mount opening. As desired, a second suture thread 76 is similarly placed through third passage and fourth passage. In this manner, when the system is desired to be removed, the exposed suture threads are pulled away from the patient to remove the system and provide reliably sutures 82 that close the incision outside the abdominal wall and that ensure the anchor and balloon attached thereto is anchored to the gastric wall. As desired, for a plurality of unique suture threads, different color threads are used to ensure the appropriate ends are tied together, such as red-to-red and blue-to-blue.

Figure 13:
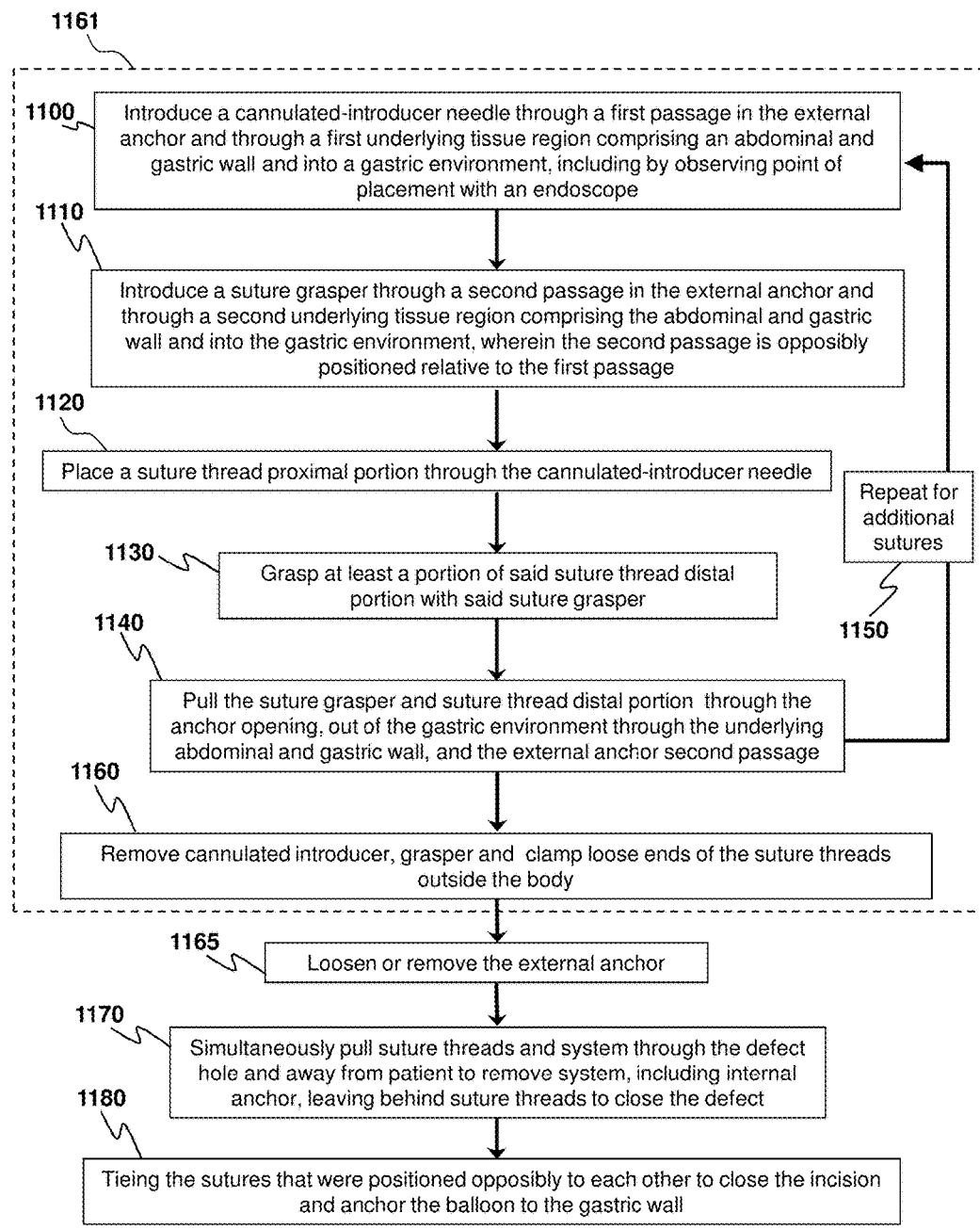
FIG. 13. Flow chart summary of a method of removing the system and securing the gastric balloon anchor to the gastric wall; and as schematically illustrated in FIGS. 7A-7C and 14-17.
Figure 14:
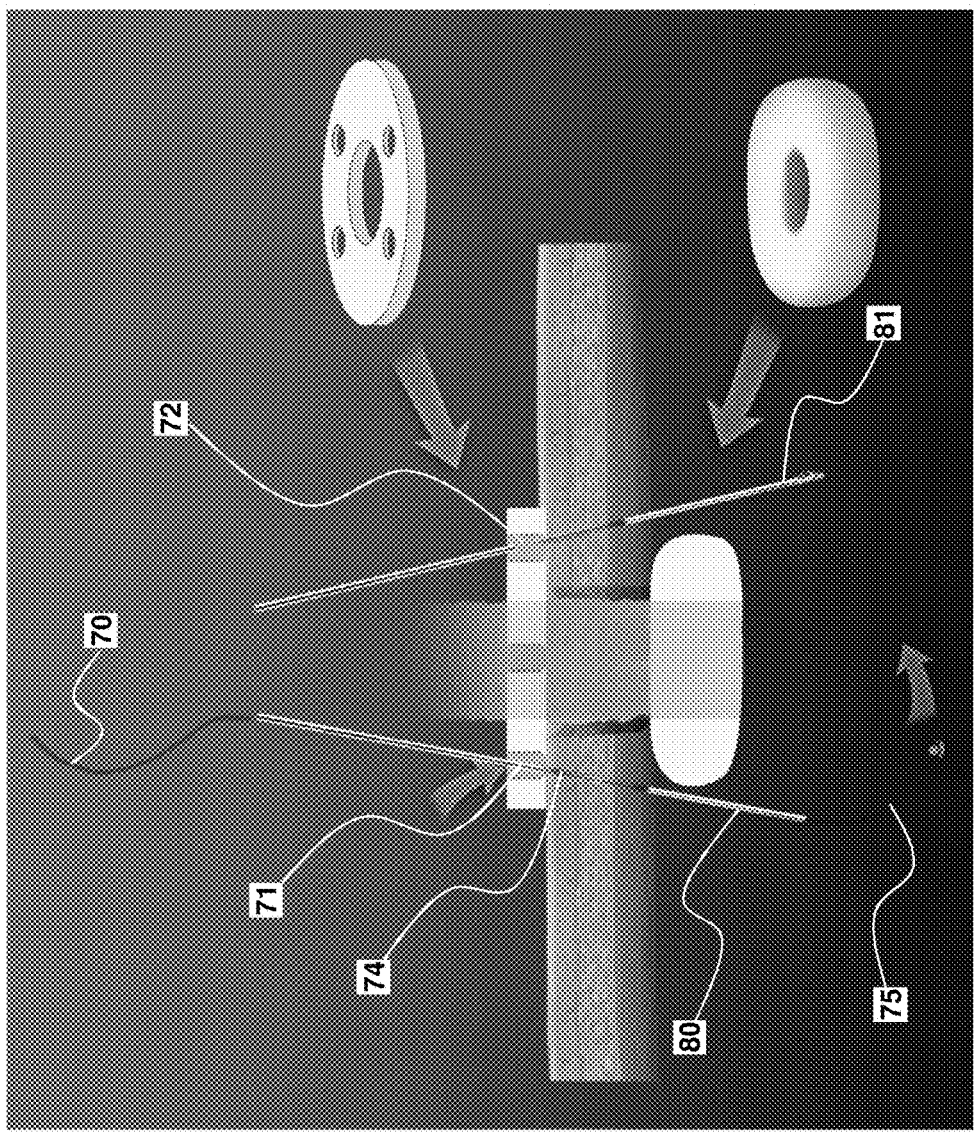
FIG. 14. Schematic illustration showing suture thread introduction through a first external anchor flange passage.
Figure 15:
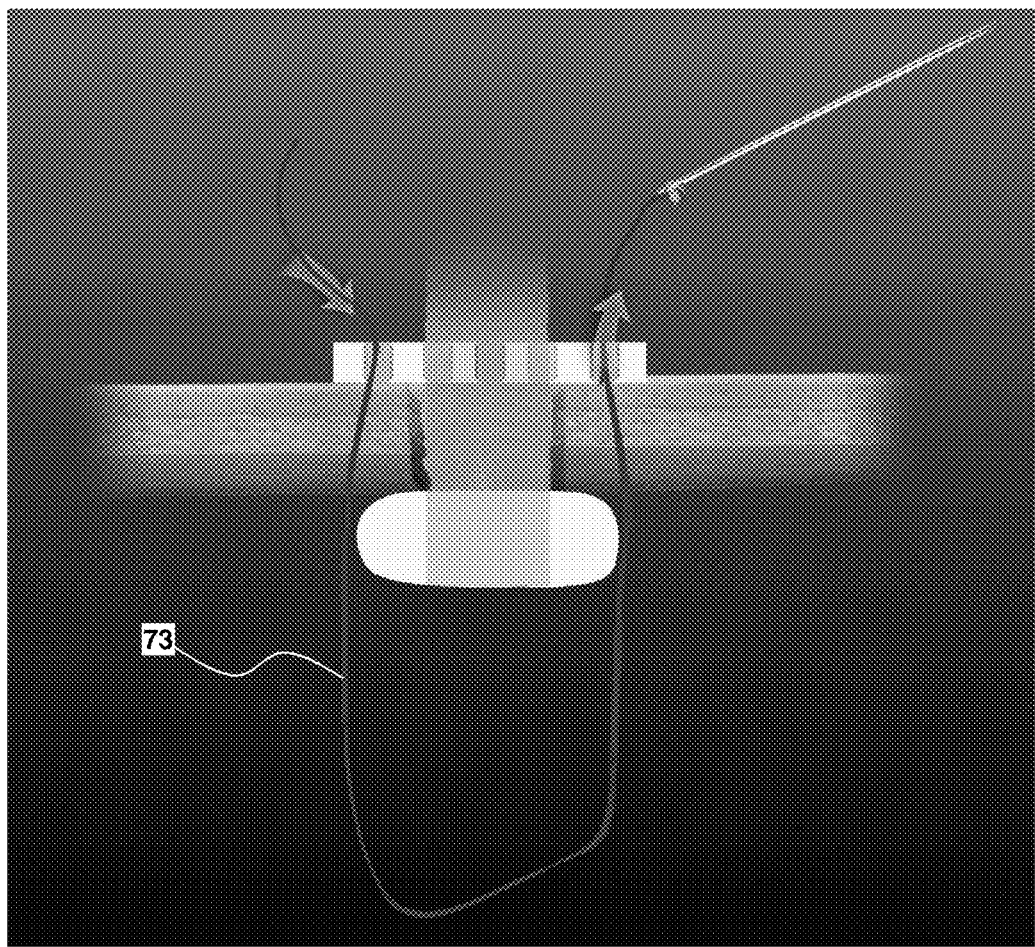
FIG. 15. The suture thread of FIG. 14 is grasped and pulled out of the patient with a grasper that traverses a second external anchor passage that is opposibly positioned relative to the first external anchor passage. Optionally, suture guide elements assist with positioning of suture threads in a desired linear position over the internal anchor outer-facing surface.
Figure 16:
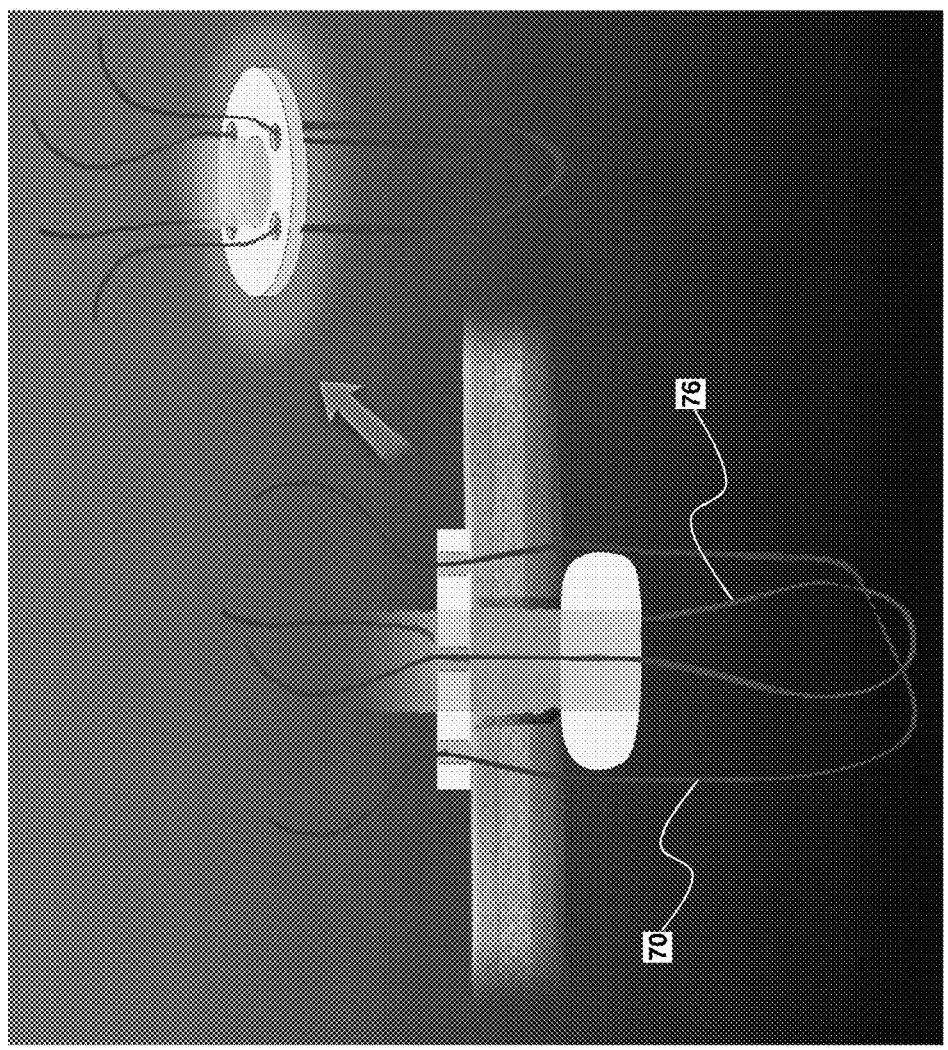
FIG. 16. The steps outlined in FIGS. 14-15 are repeated for a second suture thread.
Figure 17:
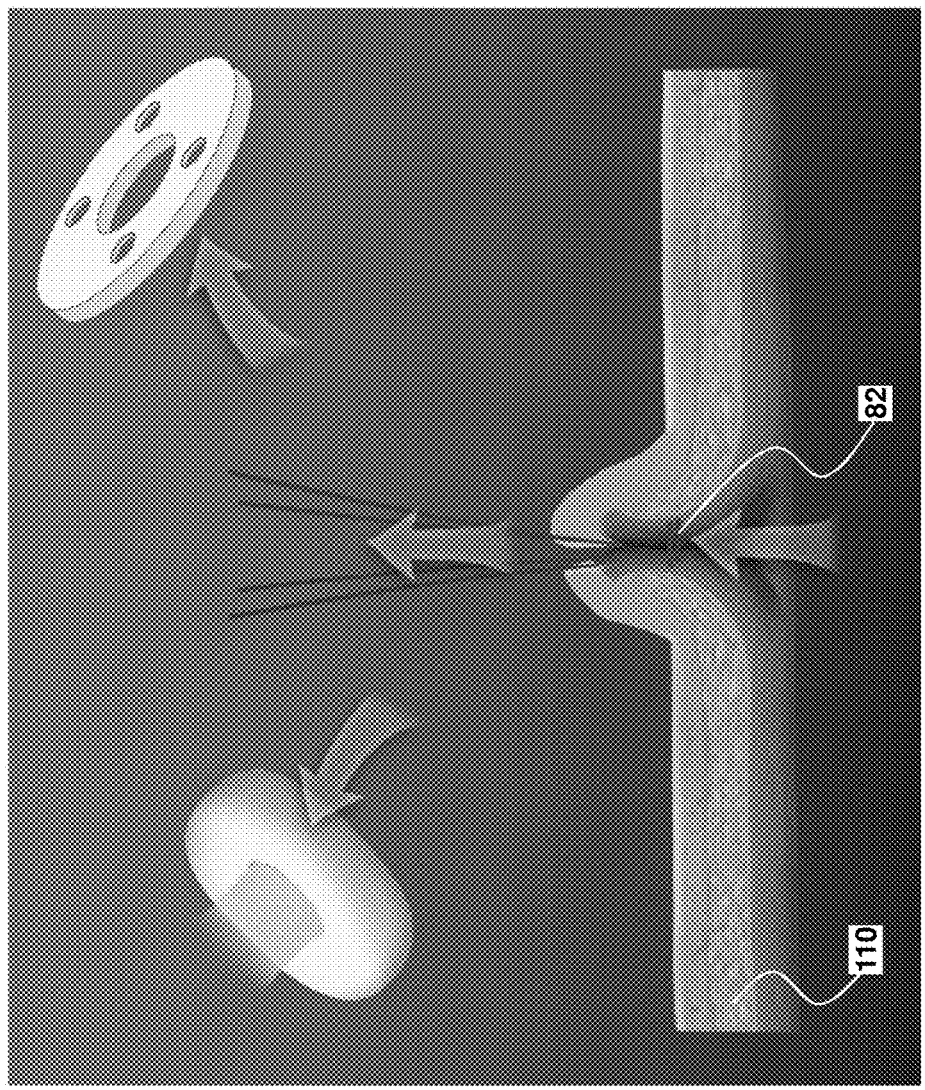
FIG. 17. The accessible suture threads are pulled so that all suture threads and the internal anchor are pulled outside the abdominal wall, thereby suturing the incision closed. The inset illustrates the opposing passages configuration through which suture threads pass.

An example of a method for removing the system in a safe and effective manner is summarized in the flow chart of FIG. 13 and corresponding illustrations FIG. 14-17. Passages 49 in the external anchor facilitate controlled suture positioning at the start of a surgical procedure. In steps 1100 and 1110, cannulated introducer needle 80 and suture grasper 81 are positioned through first passage 71 and second passage 72 (FIG. 14) and underlying tissue into the gastric space. A suture thread is grasped and pulled through passage 71 and out of passage 72, thereby providing a threaded loop around the outermost portion of the internal anchor and through an anchor opening (FIG. 15 and steps 1120 1130 and 1140). As desired, steps 1100-1140 are repeated to obtain additional suture threads at different orientations from each other (FIG. 16 and repeating step 1150). The suture thread ends are pulled away from the patient to remove the system and internal and external anchors, thereby providing sutures 82 outside the abdominal wall 110 and to secure the balloon to the gastric wall to avoid distal migration of the balloon while allowing for constrained balloon movement (FIG. 17 and steps 1160 1165 1170 1180). This method is simple and reliable, while minimizing the risk of infection or other complications associated with conventional trocar insertion methods. As illustrated in FIGS. 7A-7C, the loose presuture loops may be placed through an opening 725 in the anchor, such as an anchor mount 720, to facilitate reliable anchoring of a balloon to the gastric wall, including via an at least partially gastric-wall embedded anchor.

Example 5: System Introduction and Placement

Any one or more of the systems described herein is readily and reliably introduced to a patient. An example of one such method for introducing the system is summarized in the flow chart of FIG. 18 and corresponding illustrations FIGS. 19-24.

Figure 18:
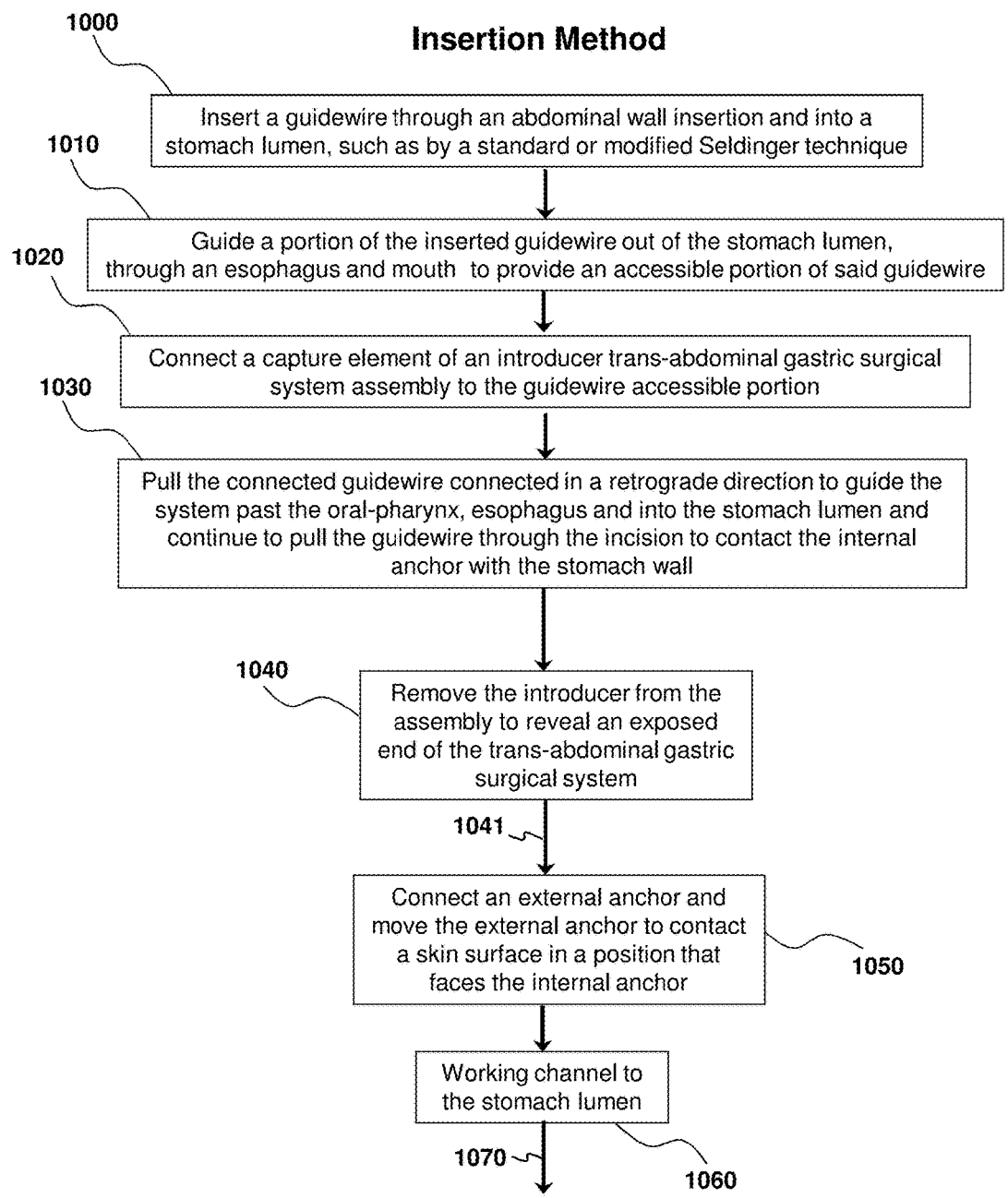
FIG. 18. Flow chart summary of system introduction to a patient and corresponding to illustrations in FIGS. 19-22.
Figure 18:
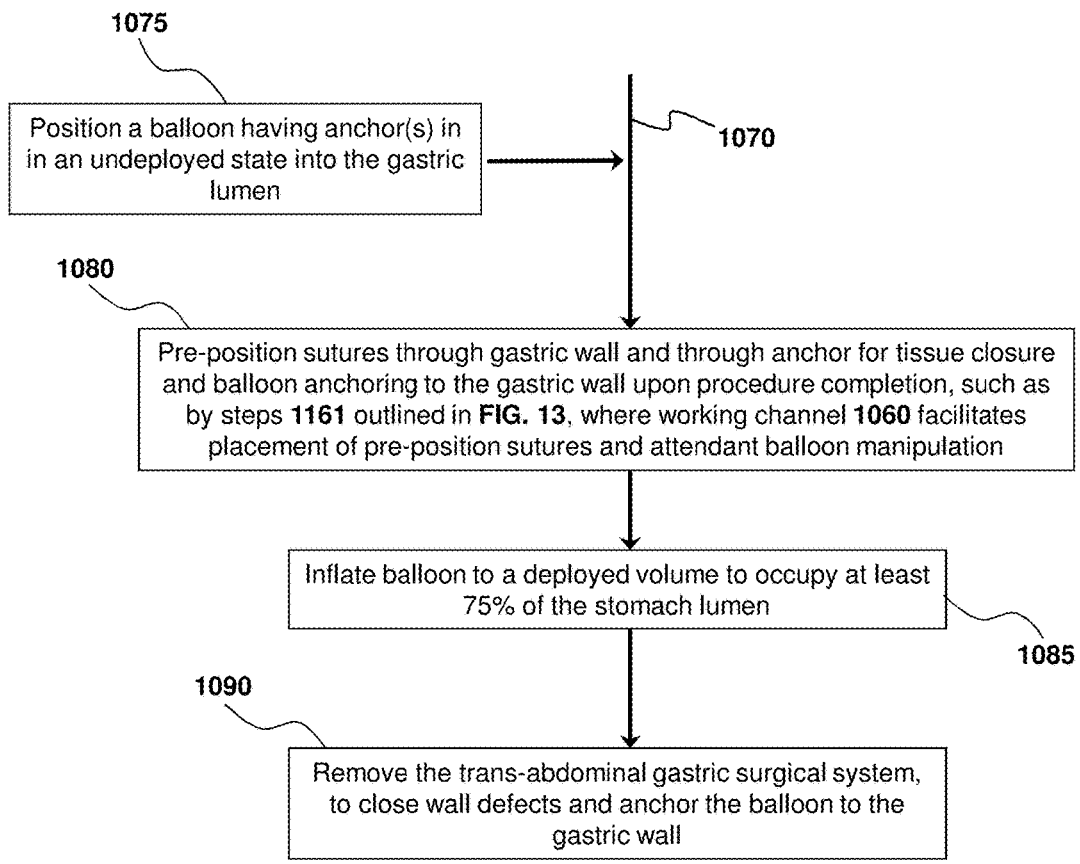
Figure 20:
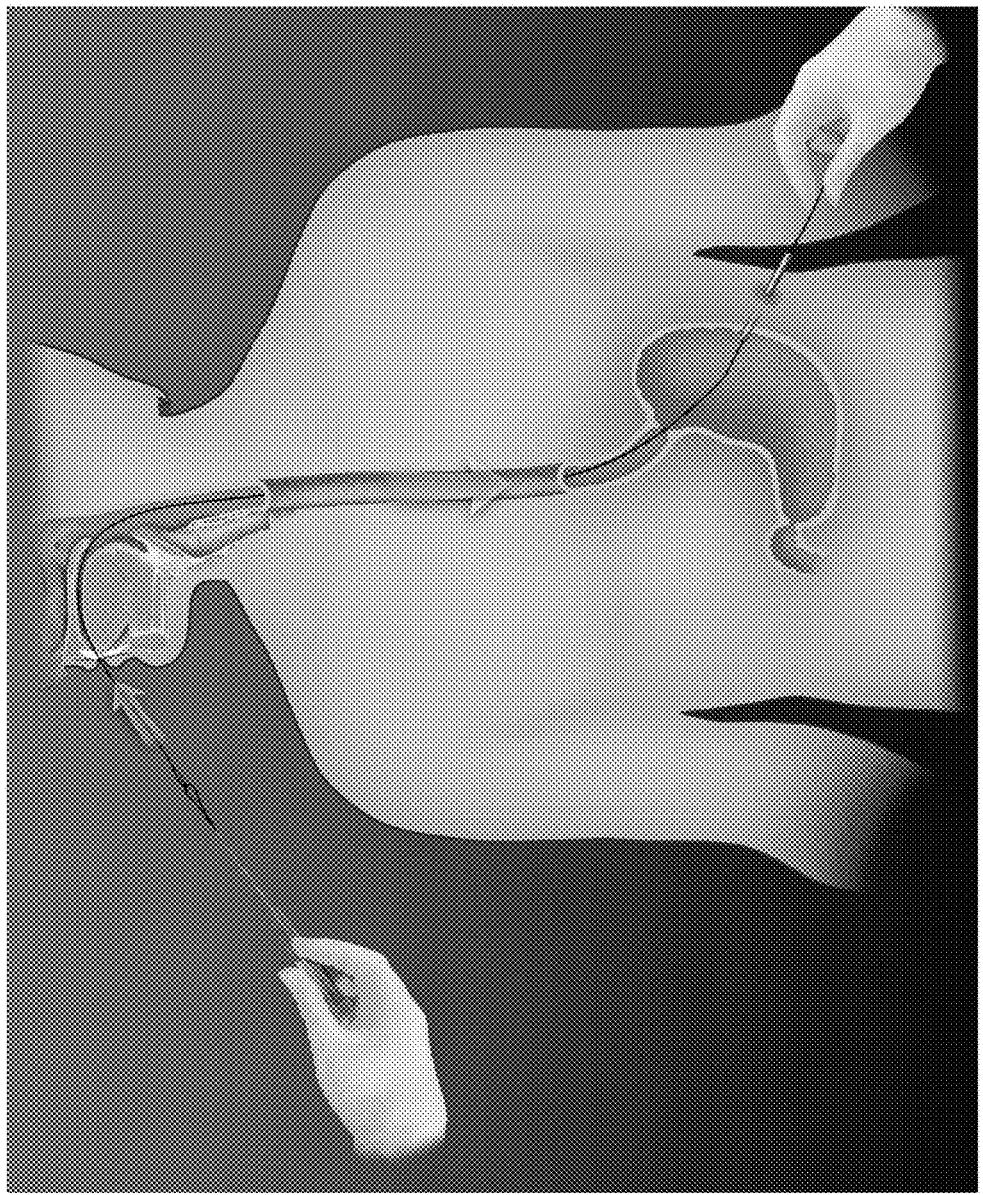
FIG. 20. Guidewire connection to an introducer-system and start of retrograde introduction at the patient's mouth FIG. 21. Continued retrograde introduction of the introducer-system to the gastric environment and positioning the system by pulling the guidewire out of the abdominal incision and forcing the introducer through the abdominal wall incision FIG. 22. External anchor and cap connection and positioning of the external anchor against an outer surface of the patient to provide reliable positioning of the system and a reliable working channel through the abdominal wall. Also illustrated is an endoscope having a fiber optic light source.
Figure 21:
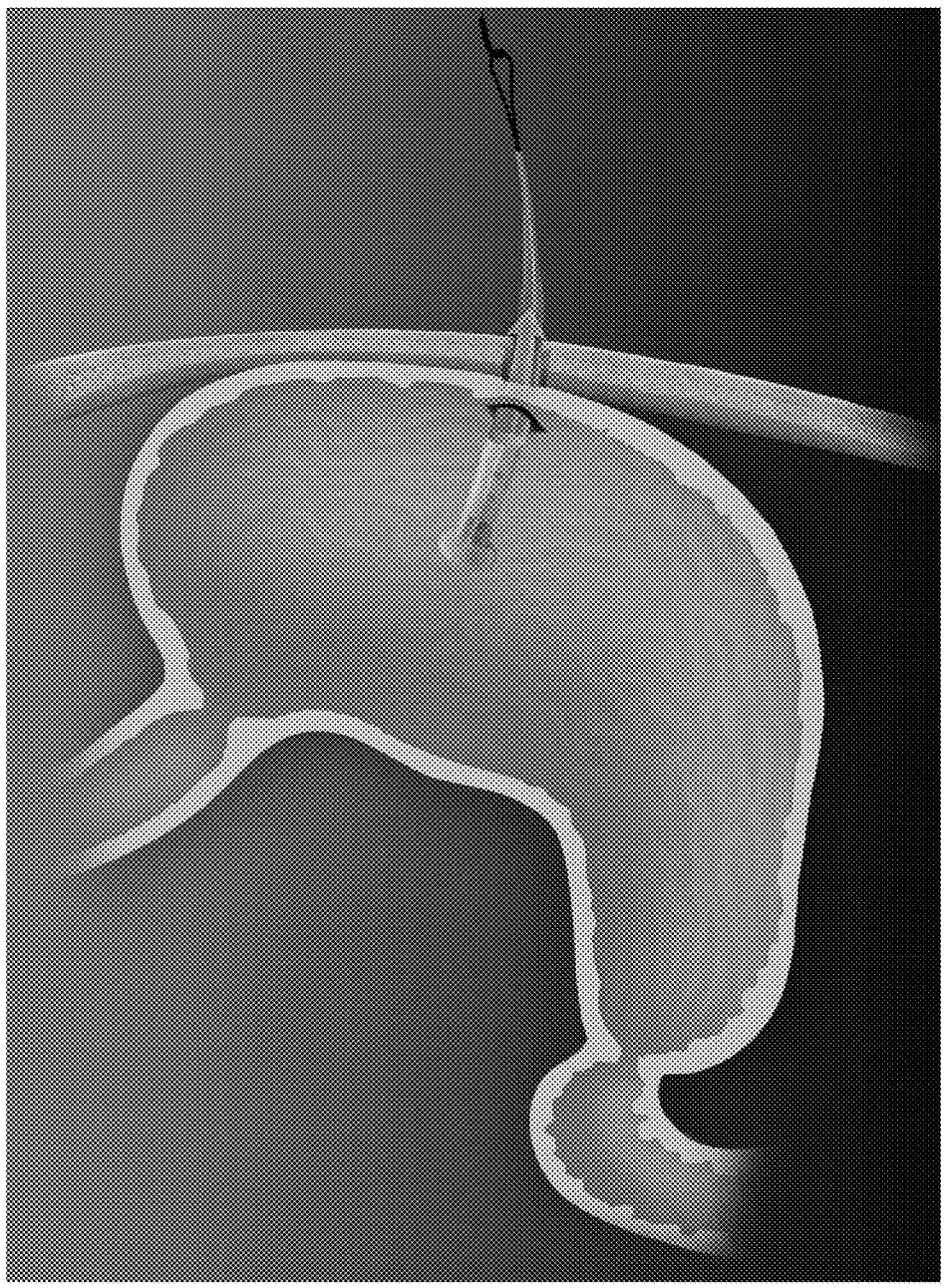
Figure 22:
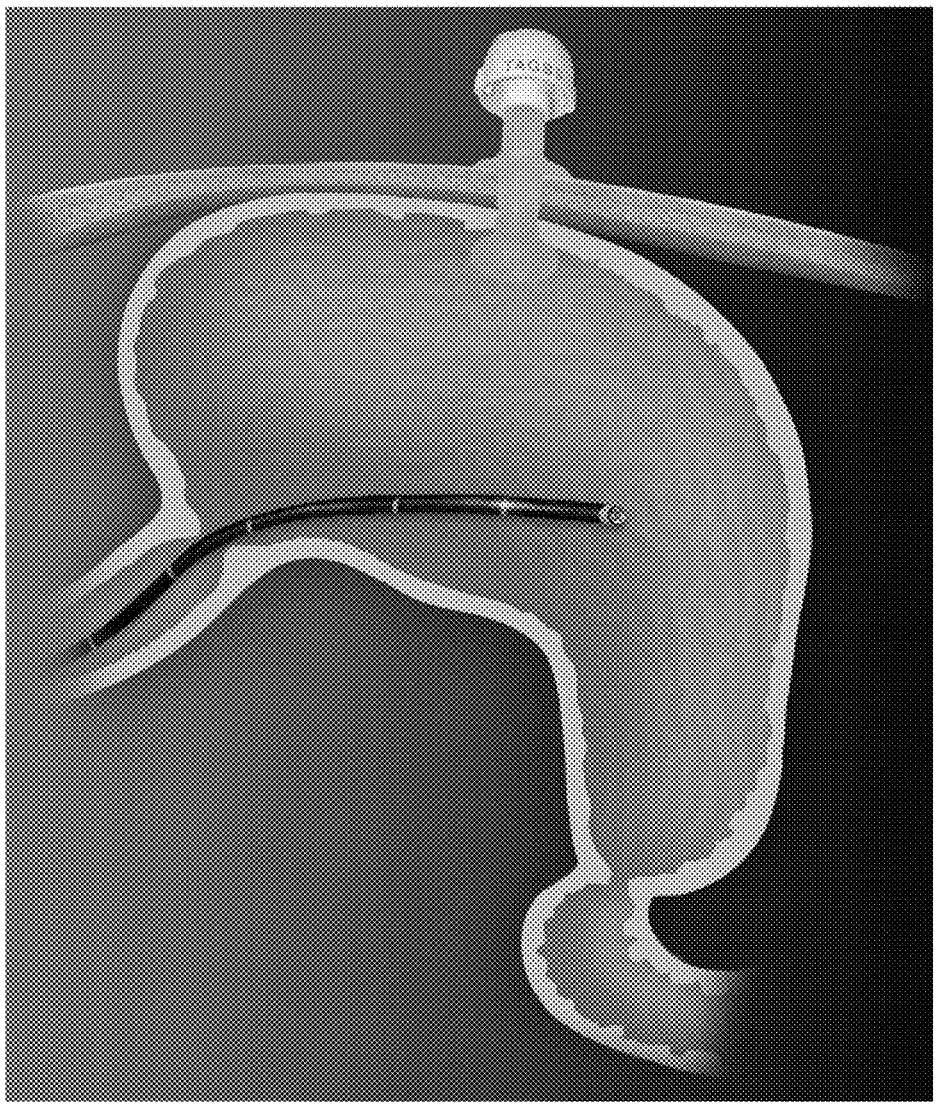

Briefly, in steps 1000, 1010 of FIG. 18 a guidewire is inserted through an abdominal wall and into the stomach lumen. For a system that will be anchored to the stomach wall, this guidewire may be directly inserted from the abdominal wall and into the stomach lumen. In step 1020, a capture element of the introducer is connected to the guidewire at one end. At the other end of the introducer the trans-abdominal gastric system is connected thereto (FIG. 20). The guidewire is then pulled in a retrograde direction, as shown in FIGS. 20-21 and step 1030 so that the internal anchor contacts the stomach wall (FIG. 22). In step 1040, the introducer is removed. The external anchor and cap (FIG. 22) are connected to the system, so that the system is reliably anchored to the abdominal wall (FIG. 22 and step 1050), thereby providing a working channel for subsequent applications, as desired. As desired, a gastric balloon may be introduced to the gastric environment via the working channel or endoscopically 1075. In addition, a gastric balloon may be manipulated, positioned and anchored with a medical instrument such as a grasper introduced to the gastric lumen via the working channel. As will be appreciated, an equivalent methodology is employed to provide system anchoring to the peritoneal surface to provide extra-luminal access relative to the stomach lumen.

Steps 1075, 1080 and 1085 relate to insertion, positioning and inflation of a gastric balloon for a weight-loss application. In step 1075, the balloon is inserted into the gastric lumen. This insertion can be by a range of methods, including with the insertion of the cannula summarized in the prior steps, such as a balloon that is integrally packaged with the internal anchor of the transabdominal gastric system, endoscopically either before or after the transabdominal gastric system is inserted, or via the cannula of the transabdominal gastric system.

To facilitate balloon positioning, a medical instrument, such as a laparoscopic grasper, is inserted into the stomach lumen via the gastric cannula working channel 1060. As desired, additional instruments and working channels may be similarly inserted, to provide device triangulation on various specific points, such as balloon anchors. The balloon is inflated and anchored to the stomach wall at a desired position 1085. As desired, the system is removed in step 1090, leaving behind suture-closed wall defects and corresponding wall-anchored inflated balloon, including by an at least partially-embedded anchor.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups are disclosed separately. When a Markush group or other grouping is used herein, all individual members of the group and all combinations and subcombinations possible of the group are intended to be individually included in the disclosure.

Every formulation or combination of components described or exemplified herein can be used to practice the invention, unless otherwise stated.

Whenever a range is given in the specification, for example, a size range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that materials, biological materials and methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A gastric balloon system for treatment of obesity in a patient comprising:
    a transabdominal gastric cannula for gastric balloon insertion or manipulation in a stomach lumen comprising:
        an outer end;
        an inner end;
        a central portion having an outer-facing surface that extends between said inner end and said outer end and an inner-facing surface that defines a lumen;
    an internal anchor connected to said inner end and having a surface shape configured to secure the system against an interior surface of a gastric wall;
    an external anchor removably and translationally connected to said cannula outer-facing surface and having a surface shape configured to secure said system against a skin surface;
    a size-varying gastric balloon configured for delivery to a stomach lumen through the transabdominal gastric cannula or endoscopically, said size-varying gastric balloon comprising:

a gastric balloon surface;
an internal volume defined by said gastric balloon surface;
a gastric balloon anchor connected to said gastric balloon surface configured to reliably position and anchor said size-varying gastric balloon in a gastric environment;
a fluid conduit having a first fluid end and a second fluid end:
wherein said first fluid end is fluidically connected to said size-varying gastric balloon internal volume and said second fluid end is positioned external to the size-varying gastric balloon internal volume;
wherein said fluid conduit is configured to introduce a fluid to said internal volume to increase said internal volume to a deployed internal volume and provide a gastric balloon deployed configuration,
said size-varying gastric balloon having an annulus in said deployed configuration configured to align in the stomach to pass food and liquid in a direction from an esophageal exit toward a pyloric sphincter.

2. The gastric balloon system of claim 1, wherein said gastric balloon anchor is connected to said transabdominal gastric cannula, thereby tethering said gastric balloon in a desired position within the stomach lumen.

3. The gastric balloon system of claim 1, wherein said fluid conduit is connected to an anterior portion of said size-varying gastric balloon and traverses said cannula lumen.

4. The gastric balloon system of claim 1, further comprising a second fluid conduit and a second transabdominal gastric cannula through which each fluid conduit independently traverses, each first fluid conduit end connected to an anterior portion of said size-varying gastric balloon with the connections separated from each other by a fluid conduit separation distance that is greater than or equal to 15 cm to provide at least two ports for inflation, deflation, or inflation and deflation.

5. The gastric balloon system of claim 1, wherein said transabdominal gastric cannula has a low profile, and after deployment to said gastric balloon deployed configuration, said transabdominal gastric cannula is retained in the patient.

6. The gastric balloon system of claim 5, wherein said fluid conduit is configured to remove a fluid from said internal volume to decrease said internal volume.

7. The gastric balloon system of claim 1, wherein said fluid conduit is connected to a fluid source external to the patient for introducing a fluid to said internal volume to control said size-varying gastric balloon shape and size, wherein said fluid is a gas, a liquid, or a gel.

8. The gastric balloon system of claim 1, wherein said fluid conduit is connected to said transabdominal gastric cannula.

9. The gastric balloon system of claim 1, wherein said annulus has an average diameter that is greater than or equal to 0.5 cm and less than or equal to 5 cm and a deployed volume that occupies at least 75% of the stomach lumen.

10. The gastric balloon system of claim 9, wherein said annulus has a length that is greater than or equal to 5 cm and less than or equal to 50 cm.

11. The gastric balloon system of claim 10, wherein said annulus is curved and during use said annulus has:
an entry end configured to be aligned and separated from a patient's esophageal exit; and
an exit end configured to be aligned and separated from a patient's pyloric sphincter.

12. The gastric balloon system of claim 1, wherein during use:
at least 75% of the stomach lumen is occupied by a deployed balloon and less than 25% of the stomach lumen is unoccupied by the deployed balloon, wherein the gastric balloon anchor mechanically connects the deployed balloon to a stomach surface to maintain a deployed balloon position relative to the gastric lumen during long-term use.

13. The gastric balloon system of claim 12, wherein during use said entry end and said exit end are substantially fixably positioned within a gastric environment by one or more gastric balloon anchors that substantially constrain gastric balloon migration.

14. The system of claim 13, wherein said gastric balloon anchor comprises a first end operably connected to said gastric balloon surface and a second end configured to connect to a suture extending from a gastric wall during use.

15. The system of claim 1, wherein said gastric balloon anchor comprises said fluid conduit connected to said internal volume, wherein said fluid conduit comprises a percutaneous catheter that passes through and is connected to said transabdominal gastric cannula.

16. The system of claim 1, further comprising an elongated sleeve configured for insertion into a portion of a patient's small intestine, said elongated sleeve having a lumen and a proximal end connected thereto, said proximal end configured for positioning at or adjacent to a pyloric sphincter and aligned with said gastric balloon annulus during use.

17. The gastric balloon system of claim 1, wherein the gastric balloon anchor comprises:
an anchor mount having an opening for receiving one or more pre-sutures to at least partially embed the anchor mount in the gastric wall;
a fastener having:
a first end configured to connect to a gastric balloon surface; and
a second end configured to connnect to an anchor ring.

18. A method of treating obesity in a patient, the method comprising the steps of:
inserting a stomach lumen working channel through an abdominal wall of the patient;
inserting a size-varying gastric balloon in an undeployed configuration into a stomach lumen, wherein said size-varying gastric balloon has an annulus;
securing said size-varying gastric balloon to a stomach wall by connecting a balloon anchor to a gastric wall, wherein said annulus is positioned in a longitudinal orientation relative to the stomach lumen; and
introducing a fluid to an internal volume of said size-varying gastric balloon to provide said size-varying gastric balloon in a deployed configuration that occupies at least 75% of the stomach lumen, wherein said annulus is substantially aligned with said esophageal and pyloric sphincters to reduce risk of a stomach blockage during use.

19. The method of claim 18, wherein said inserting the working channel step comprises:
inserting a transabdominal gastric surgical system through an abdominal wall by a retrograde introduction, said inserted transabdominal gastric surgical system having a cannula lumen with an inner end connected to an internal anchor and an outer end connected to an external anchor, with a patient's abdominal wall positioned therebetween.

20. The method of claim 19, further comprising the step of inserting a second transabdominal gastric surgical system through the abdominal wall and manipulating the introduced gastric balloon and the balloon anchors with a medical instrument that traverses the second transabdominal gastric surgical system.

21. The method of claim 19, wherein said securing step comprises:
attaching one or more gastric balloon anchors to a top portion or sidewall portion of the stomach wall to prevent distal migration of the deployed balloon in a direction toward a pyloric sphincter, wherein a one or more sutures extend from the gastric wall to connect or embed a gastric balloon anchor to or in the gastric wall and thereby accommodate constrained movement of the gastric balloon relative to the gastric wall.

22. The method of claim 18, further comprising the step of introducing a malabsorption sleeve to at least a portion of a small intestine of the patient, wherein a malabsorption sleeve inlet is positioned at or adjacent to a pyloric sphincter and substantially aligned with an exit of said annulus.

\* \* \* \* \*